US012697389B2

(12) United States Patent
Jiao et al.

(10) Patent No.: US 12,697,389 B2
(45) Date of Patent: Aug. 4, 2026

(54) USE OF DIKETONE COMPOUND IN PHOTODYNAMIC THERAPY OR DIAGNOSIS

(71) Applicant: BEIJING WHOLESOMETECH CO., LTD., Beijing (CN)

(72) Inventors: Ning Jiao, Beijing (CN); Jialiang Wei, Beijing (CN); Yameng Liu, Beijing (CN)

(73) Assignee: BEIJING WHOLESOMETECH CO., LTD., Beijing (CN)

( * ) Notice: Subject to any disclaimer, the term of this patent is extended or adjusted under 35 U.S.C. 154(b) by 964 days.

(21) Appl. No.: 17/612,145

(22) PCT Filed: May 11, 2020

(86) PCT No.: PCT/CN2020/089628
§ 371 (c)(1),
(2) Date: Nov. 17, 2021

(87) PCT Pub. No.: WO2020/233437
PCT Pub. Date: Nov. 26, 2020

(65) Prior Publication Data
US 2022/0257764 A1 Aug. 18, 2022

(30) Foreign Application Priority Data
May 17, 2019 (CN) ......................... 201910414266.3

(51) Int. Cl.

| | |
|---|---|
| ***A61P 35/00*** | (2006.01) |
| ***A61K 8/35*** | (2006.01) |
| ***A61K 8/365*** | (2006.01) |
| ***A61K 8/49*** | (2006.01) |
| ***A61K 8/69*** | (2006.01) |
| ***A61K 31/12*** | (2006.01) |
| ***A61K 31/121*** | (2006.01) |
| ***A61K 31/341*** | (2006.01) |
| ***A61K 31/444*** | (2006.01) |
| ***A61K 41/00*** | (2020.01) |
| ***A61Q 17/00*** | (2006.01) |
| ***A61Q 19/00*** | (2006.01) |
| ***A61Q 19/08*** | (2006.01) |
| ***G01N 33/574*** | (2006.01) |

(52) U.S. Cl.
CPC ............ *A61K 41/0057* (2013.01); *A61K 8/35* (2013.01); *A61K 8/365* (2013.01); *A61K 8/4926* (2013.01); *A61K 8/4973* (2013.01); *A61K 8/69* (2013.01); *A61K 31/12* (2013.01); *A61K 31/121* (2013.01); *A61K 31/341* (2013.01); *A61K 31/444* (2013.01); *A61P 35/00* (2018.01); *A61Q 17/005* (2013.01); *A61Q 19/00* (2013.01); *A61Q 19/08* (2013.01); *G01N 33/574* (2013.01); *A61K 2800/81* (2013.01)

(58) Field of Classification Search
CPC ...... A61K 8/365; A61K 8/35; A61K 41/0057; A61P 35/00
See application file for complete search history.

(56) References Cited

U.S. PATENT DOCUMENTS

| | | | | |
|---|---|---|---|---|
| 2009/0156552 A1* | 6/2009 | Cooper | A61P 43/00 514/185 |
| 2013/0315834 A1 | 11/2013 | Praveen et al. | |
| 2017/0021021 A1 | 1/2017 | Kamaev et al. | |
| 2018/0000753 A1 | 1/2018 | Tønnesen et al. | |

FOREIGN PATENT DOCUMENTS

| | | |
|---|---|---|
| JP | 2018526341 | 9/2018 |
| WO | 2012039685 A1 | 3/2012 |
| WO | WO 2012/039685 * | 3/2012 |
| WO | 2016108083 A1 | 7/2016 |
| WO | WO 2017/200194 * | 11/2017 |

OTHER PUBLICATIONS

Stephen et. al. (World Journal of Pharmacy and Pharmaceutical Sciences (2014) 3:1630-1647). (Year: 2014).*
Fliss et. al. (Can. J. Biochem (1979) 57:1267-1272). (Year: 1979).*
Makinen et. al. (Eur. J. Biochem. (1982) 123:171-178). (Year: 1982).*
English Translation of International Search Report and Written Opinion mailed Aug. 10, 2020 in corresponding International Patent Application No. PCT/CN2020/089628.
Makinen, et al., "Photochemical Inactivation of Lactoperoxidase Sensitized by Carbonyl Compounds"; European Journal of Biochemistry, vol. 123, Dec. 31, 1982, paragraphs 171-178.
Makinen, et al., "Photochemical Inactivation of Aeromonas Aminopeptidase by 2, 3-Butanedione", The Journal of Biological Chemistry, vol. 257, No. 4, Feb. 25, 1982, pp. 1267-1272.

(Continued)

*Primary Examiner* — Marcos L Sznaidman
(74) *Attorney, Agent, or Firm* — Polsinelli PC

(57) ABSTRACT

The disclosure belongs to the technical field of medicine, and relates to use of a diketone compound in photodynamic therapy or diagnosis. Particularly, the disclosure relates to use of a compound of formula (I), pharmaceutically acceptable salt or ester, prodrug, stereoisomer, hydrate, solvate or crystal form of the compound, metabolite of each of them, or any combination or mixture thereof in preparation of a drug or a reagent. The drug or the reagent is used for photodynamic therapy or photodynamic diagnosis of a disease or is used for skin beauty by means of photodynamic therapy.

(I)

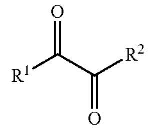

13 Claims, 7 Drawing Sheets

(56) References Cited

OTHER PUBLICATIONS

Fliss, et al., "2, 3-Butanedione as a photosensitizing agent: application to alpha-amino acids and alpha-chymotrypsin" Can J. Biochem, vol. 57, Dec. 31, 1979, pp. 1267-1272.
Makinen, et al., "Photochemical inactivation of Aeromonas aminopeptidase", Febs Letters, vol. 131, No. 1, Aug. 31, 1981, pp. 165-168.
Li et al., "Clinical Application and Research Progress of Photosensitizer"; Chinese Journal of Laser Medicine & Surgery, vol. 22, No. 05, Oct. 31, 2013, pp. 282-288 (English Abstract only).
Liu et al., "Photosensitizer Used in Clinical Photodynamic Therapy for Cancer", Chinese Journal of Applied Chemistry, vol. 30, No. 12, Dec. 31, 2013, pp. 1386-1392 (English Abstract only).
English Translation of 1st Office Action in corresponding China Application No. 201910414266.3 (7 pages).
English Translation of 2nd Office Action in corresponding China Application No. 201910414266.3 (11 pages).
Justiniano et al., "Identification of glycolysis-derived α-dicarbonyl metabolites as the smallest known endogenous UVA-photosensitizers in human skin cells and reconstructed epidermis," Journal of Investigative Dermatology (2015), vol. 135 Abstract Only (1 page).
Office Action issued Dec. 25, 2023 in corresponding Japanese Patent Application No. 2021-568748 (Original JP Office Action and English translation, totaled 9 pages).
Kashiwabara, T. et al. "Synthesis of 1,2-Diketones by the Transition Metal-Catalyst-Free Reaction of α-Oxo Acid Chlorides or Oxalyl Chloride with Organostannanes" J. Org. Chem. 2009, 74, 10, 3958-3961.
European Search Report regarding EP Application No. 20809557.0 dated Jul. 27, 2023, 8 pages.
Abrahamse, H. et al., New photosensitizers for photodynamic therapy, Biochemical Journal, 2016, vol. 473, No. 4, pp. 347-364.
Office Action issued Jan. 29, 2026 for Japanese Application No. 2024-204908, 9 pages.

* cited by examiner

USE OF DIKETONE COMPOUND IN PHOTODYNAMIC THERAPY OR DIAGNOSIS

CROSS REFERENCE TO RELATED APPLICATIONS

The present application is the U.S. National Phase under 35 U.S.C. § 371 of International Application No. PCT/CN2020/089628, filed May 11, 2020, which claims the priority of the Chinese patent application filed with the Chinese Patent Office on May 17, 2019, with the application number CN201910414266.3 and the invention title of "Use of diketone compound in photodynamic therapy or diagnosis", the entire contents of both of which are herein incorporated by reference.

TECHNICAL FIELD

The disclosure belongs to the technical field of drugs, and relates to use of a diketone compound in photodynamic therapy or diagnosis.

BACKGROUND

Photodynamic therapy is a photochemotherapy, which is based on sensitization with a photosensitizer to induce oxygen to produce reactive oxygen species (ROS) represented by singlet oxygen, which can kill tumor cells, pathogenic microorganisms or the like to achieve the purpose of treating diseases. The photodynamic therapy is a new therapy that has been used in some clinical treatments, including treatments of tumors, condyloma acuminatum, acne and port-wine stains. Compared with traditional therapies for tumors, the photodynamic therapy has significant advantages such as convenient operation, high selectivity, and few side effects. In addition, the photodynamic therapy can also be used for skin beauty. Photodynamic diagnosis refers to the characteristic spectrum of a photosensitizer that has an affinity to diseased tissues is used to diagnose a disease under the action of light. The photodynamic diagnosis has been used in the diagnosis of tumors, condyloma acuminatum, acne and port wine stains.

Basic elements of the photodynamic therapy or diagnosis include oxygen, photosensitizer and light. The hotosensitizer is the key to the photodynamic therapy or diagnosis. An ideal photosensitizer should be non-toxic, cheap and easily available, has good photochemical properties and can be metabolized quickly. Currently, the most widely used in clinical research is photosensitizers based on a structure of porphyrin and/or phthalocyanine. However, due to the existence of the large n-conjugated ring system of this type of photosensitizer, there is a strong π-π stacking effect among molecules of the photosensitizer, which causes porphyrin and/or phthalocyanine molecules to easily aggregate and reduce their photochemical efficiency, thus greatly limiting the clinical application of the photosensitizer. Therefore, seeking a novel photosensitizer molecule with good photochemical properties will help to promote the clinical application of photodynamic therapy or diagnosis, which not only has important research significance, but also has potential application value.

SUMMARY

Through in-depth research, the inventor of the disclosure has inventively discovered that certain diketone compounds induce oxygen to produce singlet oxygen and/or peroxy free radicals and other reactive oxygen species after being excited by light, thereby exhibiting significant anti-tumor effect, anti-microorganism activity and immune enhancement effect. Therefore, they can be used for photodynamic therapy or photodynamic diagnosis of a disease, and can also be used for skin beauty by photodynamic therapy, thereby providing the following disclosure.

According to one aspect, the disclosure provides use of a compound of formula (I), or a pharmaceutically acceptable salt or ester, prodrug, stereoisomer, hydrate, solvate or crystal form of the compound, metabolite of each of them, or any combination or mixture thereof in preparation of a drug or a reagent, wherein the drug or the reagent is used for photodynamic therapy or photodynamic diagnosis of a disease, or is used for skin beauty by means of the photodynamic therapy.

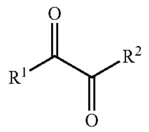

(I)

wherein $R^1$ and $R^2$ are each independently a linear or branched alkyl with 1 to 6 carbon atoms, a halogenated linear or branched alkyl with 1 to 6 carbon atoms, a hydroxyl group, or the following groups optionally substituted with one or more (e.g., 2, 3, 4, or 5) same or different substituents: aryl with 6 to 14 carbon atoms, 5- to 6-membered heteroaryl, 5- to 6-membered heterocyclyl, and 3- to 6-membered cycloalkyl, wherein the substituents are each independently a hydroxyl group, a carboxyl group, a sulfonic group, a halogen (such as fluorine, chlorine, bromine or iodine) atom, an amino group, a mercapto group, a nitro group, —C(O)O-(linear or branched alkyl with 1 to 4 carbon atoms), $—S(O)_2O$-(linear or branched alkyl with 1 to 4 carbon atoms), or —O-(linear or branched alkyl with 1 to 4 carbon atoms).

In some embodiments, the linear or branched alkyl with 1 to 6 carbon atoms is a linear or branched alkyl with 1 to 4 carbon atoms.

In some embodiments, the linear or branched alkyl with 1 to 4 carbon atoms is methyl, ethyl, n-propyl, isopropyl, n-butyl, sec-butyl, isobutyl, or tert-butyl.

In some embodiments, the aryl with 6 to 14 carbon atoms is a phenyl or a naphthyl.

In some embodiments, the halogenated linear or branched alkyl with 1 to 6 carbon atoms is a fluoro-, chloro-, bromo- or iodo-linear or branched alkyl with 1 to 6 carbon atoms. In some embodiments, the halogenated linear or branched alkyl with 1 to 6 carbon atoms is a halogenated linear or branched alkyl with 1 to 4 carbon atoms, such as a fluoromethyl, a bromomethyl, a chloromethyl, a fluoroethyl, a bromoethyl, or a chloroethyl.

As used herein, "halogenated" includes substitution with one or more (e.g., 2, 3, 4, or 5) halogen atoms (e.g., fluorine, chlorine, bromine, or iodine).

In some embodiments, the fluoromethyl is $—CH_2F$, $—CHF_2$, or $—CF_3$. In some embodiments, the bromomethyl is $—CH_2Br$, $—CHBr_2$, or $—CBr_3$.

In some embodiments, the chloromethyl is $—CH_2Cl$, $—CHCl_2$, or $—CCl_3$.

In some embodiments, the fluoroethyl is a monofluoroethyl, a difluoroethyl, a trifluoroethyl, a tetrafluoroethyl, or a perfluoroethyl.

In some embodiments, the bromoethyl is a monobromoethyl, a dibromoethyl, a tribromoethyl, a tetrabromoethyl, or a perbromoethyl.

In some embodiments, the chloroethyl is a monochloroethyl, a dichloroethyl, a trichloroethyl, a tetrachloroethyl, or a perchloroethyl.

In some embodiments, the 5- to 6-membered heteroaryl contains 1 to 3 ring atoms selected from nitrogen, oxygen, and sulfur. In some embodiments, the 5- to 6-membered heteroaryl is a furyl, thienyl, a pyrrolyl, an oxazolyl, an isoxazolyl, an imidazolyl, a pyridyl, a pyrimidinyl, a pyridazinyl, or a pyrazinyl.

In some embodiments, the 5- to 6-membered heterocyclyl contains 1 to 3 ring atoms of nitrogen, oxygen, and sulfur. In some embodiments, the 5- to 6-membered heterocyclyl is an aziridinyl, a diaziridinyl, an azetidinyl, a dioxanyl, a dioxolane, a tetrahydrofuranyl, a pyrrolidinyl, an imidazolidinyl, a pyrazolidinyl, a tetrahydrothienyl, a piperidinyl, a piperazinyl, a morpholinyl, a hexahydropyrimidinyl, or a hexahydropyridazinyl. If the heteroaryl or heterocyclyl contains multiple heteroatoms, the multiple heteroatoms may be the same or different.

In some embodiments, $R^1$ represents a linear or branched alkyl with 1 to 4 carbon atoms (e.g., methyl or ethyl) or an aryl with 6 to 14 carbon atoms (e.g., phenyl).

In some embodiments, $R^2$ represents a linear or branched alkyl with 1 to 4 carbon atoms (e.g., methyl, ethyl, n-propyl, isopropyl, n-butyl, or tert-butyl), a halogenated linear or branched alkyl with 1 to 4 carbon atoms (e.g., bromomethyl or bromoethyl), or hydroxy.

In some embodiments, $R^1$ represents a linear or branched alkyl with 1 to 4 carbon atoms (e.g., methyl or ethyl), and $R^2$ represents a linear or branched alkyl with 1 to 4 carbon atoms (e.g., methyl, ethyl, n-propyl, isopropyl, n-butyl, or tert-butyl).

In some embodiments, $R^1$ represents a linear or branched alkyl with 1 to 4 carbon atoms (e.g., methyl or ethyl) or a phenyl, and $R^2$ represents hydroxy.

In some embodiments, $R^1$ represents a linear or branched alkyl with 1 to 4 carbon atoms (e.g., methyl or ethyl), and $R^2$ represents a halogenated linear or branched alkyl with 1 to 4 carbon atoms (e.g., bromomethyl).

In some embodiments, $R^1$ and $R^2$ each represent a phenyl, and the phenyl is optionally substituted with one or more substituents which may be the same or different.

In some embodiments, $R^1$ and $R^2$ are each independently a nitrogen-containing 5- to 6-membered heteroaryl, and the nitrogen-containing 5- to 6-membered heteroaryl is optionally substituted with one or more substituents which may be the same or different.

In this context, "optionally substituted with" means that it may or may not be substituted.

In some embodiments, $R^1$ and $R^2$ are same group.

In some embodiments, $R^1$ and $R^2$ are different groups.

In some embodiments, the compound is selected from the following:

| No. | Structural formula |
| --- | --- |
| BJMU-201 | 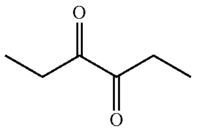 |

-continued

| No. | Structural formula |
| --- | --- |
| BJMU-202 | 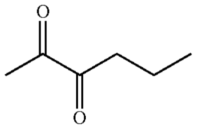 |
| BJMU-203 | 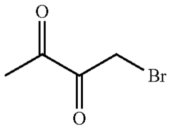 |
| BJMU-204 | 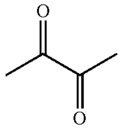 |
| BJMU-205 | 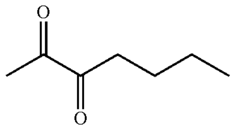 |
| BJMU-206 | 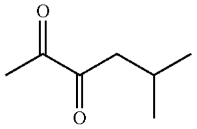 |
| BJMU-207 | 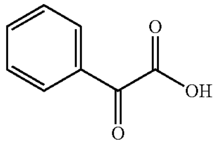 [SMILES: O=C(O)C(=O)c1ccccc1] |
| BJMU-208 | 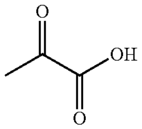 |
| BJMU-209 | 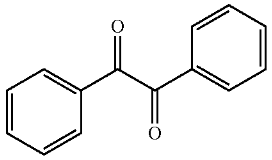 [SMILES: O=C(C(=O)c1ccccc1)c1ccccc1] |
| BJMU-210 | 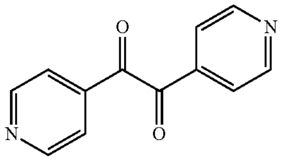 [SMILES: O=C(C(=O)c1ccncc1)c1ccncc1] |
| BJMU-211 | 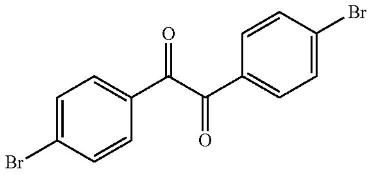 [SMILES: O=C(C(=O)c1ccc(Br)cc1)c1ccc(Br)cc1] |

-continued

| No. | Structural formula |
|---|---|
| BJMU-212 | 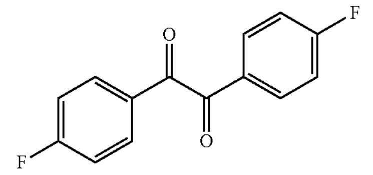 [SMILES: O=C(C(=O)c1ccc(F)cc1)c1ccc(F)cc1] |
| BJMU-213 | 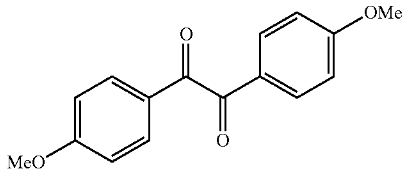 [SMILES: COc1ccc(C(=O)C(=O)c2ccc(OC)cc2)cc1] |
| BJMU-214 | 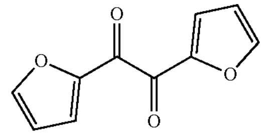 [SMILES: O=C(C(=O)c1ccco1)c1ccco1] |

In some embodiments, the compound, or the pharmaceutically acceptable salt or ester, prodrug, stereoisomer, hydrate, solvate or crystal form of the compound, metabolite of each of them, or any combination or mixture thereof is used as a photosensitizer for photodynamic therapy or photodynamic diagnosis.

In some embodiments, the photodynamic therapy is performed by a method including the following steps:

step I: applying the compound, the pharmaceutically acceptable salt or ester, prodrug, stereoisomer, hydrate, solvate or crystal form of the compound, metabolite of each of them, or any combination or mixture thereof according to any of the above to a subject; and step II: irradiating the subject with light.

In some embodiments, in step I, the compound, the pharmaceutically acceptable salt or ester, prodrug, stereoisomer, hydrate, solvate or crystal form of the compound, metabolite of each of them, or any combination or mixture thereof are applied to the subject in a suitable way, e.g., by way of dripping, oral administration, perfusion, smearing, or injection.

In some embodiments, in step I, the compound, the pharmaceutically acceptable salt or ester, prodrug, stereoisomer, hydrate, solvate or crystal form of the compound, metabolite of each of them, or any combination or mixture thereof are used in from of a solution. In some embodiments, the solution is an aqueous solution. In some embodiments, the solution is a solution using physiological saline as a solvent. In some embodiments, the solution has a concentration of 0.5 wt % to 3 wt % (e.g., 0.5 wt % to 1 wt %, 1 wt % to 2 wt %, or 2 wt % to 3 wt %).

In step II, a single-wavelength light or a mixed light may be used.

In some embodiments, in step II, at least part of the wavelength of the light is in a range of 10 nm to 1 mm, for example, in one or more of a range of 10 nm to 380 nm, a range of 380 nm to 780 nm, a range of 780 nm to 3 μm, a range of 3 μm to 30 μm, and a range of 30 μm to 1 mm. In some embodiments, at least part of the wavelength of the light is in a range of 400 nm to 480 nm. In some embodiments, at least part of the wavelength of the light is in a range of 450 nm to 480 nm.

In some embodiments, in step II, the irradiation is carried out for 1 s to 12 h, for example, 1 s to 10 s, 10 s to 100 s, 100 s to 200 s, 200 s to 500 s, or 500 s to 900 s, for example, 1 min to 10 min, 10 min to 30 min, or 30 min to 60 min, for example, 1 h to 2 h, 2 h to 5 h, or 5 h to 12 h.

In some embodiments, in step II, the irradiation is carried out at a light intensity of 1-2000 mW/cm$^2$, (e.g., 1 to 15 mW/cm$^2$, 15 mW/cm$^2$ to 50 mW/cm$^2$, 50 mW/cm$^2$ to 100 mW/cm$^2$, 100 mW/cm$^2$ to 200 mW/cm$^2$, 200 mW/cm$^2$ to 300 mW/cm$^2$, 300 mW/cm$^2$ to 500 mW/cm$^2$, 500 mW/cm$^2$ to 1000 mW/cm$^2$, 1000 mW/cm$^2$ to 1500 mW/cm$^2$, or 1500 mW/cm$^2$ to 2000 mW/cm$^2$.

In some embodiments, step II includes: irradiating the subject's body or surface at a desired treatment site (for example, a site where a lesion occurs) with light, or irradiating the subject's whole body with light.

According to another aspect, the disclosure provides a method for diagnosing or treating a disease in a subject, including a step of using the compound, the pharmaceutically acceptable salt or ester, prodrug, stereoisomer, hydrate, solvate or crystal form of the compound, metabolite of each of them, or any combination or mixture thereof according to any of the above as a photosensitizer.

In some embodiments, the method includes step I and step II as defined in any one of the above.

According to another aspect, the disclosure provides a method for performing skin beauty on a subject, including a step of using the compound, the pharmaceutically acceptable salt or ester, prodrug, stereoisomer, hydrate, solvate or crystal form of the compound, metabolite of each of them, or any combination or mixture thereof according to any of the above as a photosensitizer. In some embodiments, the skin beauty is for non-therapeutic purpose.

In some embodiments, the method includes the following steps:

Step I': applying the compound, the pharmaceutically acceptable salt or ester, prodrug, stereoisomer, hydrate, solvate or crystal form of the compound, metabolite of each of them, or any combination or mixture thereof according to any of the above to skin of a subject; and step II': irradiating the skin with light. In step II', a single-wavelength light or a mixed light may be used.

In some embodiments, in step II', at least part of the wavelength of the light is in a range of 10 nm to 1 mm, for example, in one or more of a range of 10 nm to 380 nm, a range of 380 nm to 780 nm, a range of 780 nm to 3 μm, a range of 3 m to 30 μm, and a range of 30 μm to 1 mm. In some embodiments, at least part of the wavelength of the light is in a range of 400 nm to 480 nm. In some embodiments, at least part of the wavelength of the light is in a range of 450 nm to 480 nm.

In some embodiments, in step II', the irradiation is carried out for 1 s to 12 h, for example, 1 s to 10 s, 10 s to 100 s, 100 s to 200 s, 200 s to 500 s, or 500 s to 900 s, for example, 1 min to 10 min, 10 min to 30 min, or 30 min to 60 min, for example, 1 h to 2 h, 2 h to 5 h, or 5 h to 12 h.

In some embodiments, in step II', the irradiation is carried out at a light intensity of 1-2000 mW/cm$^2$, (e.g., 1 to 15 mW/cm$^2$, 15 mW/cm$^2$ to 50 mW/cm$^2$, 50 mW/cm$^2$ to 100 mW/cm$^2$, 100 mW/cm$^2$ to 200 mW/cm$^2$, 200 mW/cm$^2$ to 300 mW/cm$^2$, 300 mW/cm$^2$ to 500 mW/cm$^2$, 500 mW/cm$^2$ to 1000 mW/cm$^2$, 1000 mW/cm$^2$ to 1500 mW/cm$^2$, or 1500 mW/cm$^2$ to 2000 mW/cm$^2$.

Further, the method of skin beauty according to the disclosure may also be used in combination with another skin beauty method. For example, it can be used in combination with a skin beauty method (e.g., photorejuvenation)

using a red and blue light therapeutic apparatus to relieve a skin symptom related to microorganism infection (such as acnes) and simultaneously repair dermal tissue.

According to another aspect, the disclosure provides use of the compound, the pharmaceutically acceptable salt or ester, prodrug, stereoisomer, hydrate, solvate or crystal form of the compound, metabolite of each of them, or any combination or mixture thereof according to any of the above in combination with light in treatment or diagnosis of a disease in a subject.

The light may be a single-wavelength light or a mixed light.

In some embodiments, at least part of the wavelength of the light is in a range of 10 nm to 1 mm, for example, in one or more of a range of 10 nm to 380 nm, a range of 380 to 780 nm, a range of 780 nm to 3 μm, a range of 3 μm to 30 μm, and a range of 30 μm to 1 mm. In some embodiments, at least part of the wavelength of the light is in a range of 400 nm to 480 nm. In some embodiments, at least part of the wavelength of the light is in a range of 450 nm to 480 nm.

In some embodiments, the treatment is performed by a method including step I and step II as defined in any one of the above.

According to another aspect, the disclosure provides use of the compound, the pharmaceutically acceptable salt or ester, prodrug, stereoisomer, hydrate, solvate or crystal form of the compound, metabolite of each of them, or any combination or mixture thereof according to any of the above in combination with light in skin beauty. In some embodiments, the skin beauty is for non-therapeutic purpose.

The light may be a single-wavelength light or a mixed light.

In some embodiments, at least part of the wavelength of the light is in a range of 10 nm to 1 mm, for example, in one or more of a range of 10 nm to 380 nm, a range of 380 to 780 nm, a range of 780 nm to 3 μm, a range of 3 μm to 30 μm, and a range of 30 μm to 1 mm. In some embodiments, at least part of the wavelength of the light is in a range of 400 nm to 480 nm. In some embodiments, at least part of the wavelength of the light is in a range of 450 nm to 480 nm.

In some embodiments, the skin beauty is performed by a method including step I' and step II' as defined in any one of the above.

The compound, the pharmaceutically acceptable salt or ester, prodrug, stereoisomer, hydrate, solvate or crystal form of the compound, metabolite of each of them, or any combination or mixture thereof selected in the disclosure may be used for treating or diagnosing a disease, in a subject, of (i) a tumor and its concurrent disease;

(ii) a disease related to microorganism or parasite infection; and (iii) an immune-related disease;

In some embodiments, the tumor and their its disease is selected from breast cancer, melanoma, meningioma, soft tissue sarcoma, salivary gland tumor, primary liver cancer, intraspinal tumor, mediastinal tumor, brain cancer, bone cancer, penile cancer, osteosarcoma, intracranial tumor, tongue cancer, maxillary sinus cancer, thyroid cancer, malignant lymphoma, multiple myeloma, pituitary adenoma, testicular tumor, non-Hodgkin's lymphoma, bladder cancer, leukemia, gastric cancer, nasopharyngeal cancer, laryngeal cancer, oral cancer, esophageal cancer, lung cancer, kidney cancer, cervical cancer, choriocarcinoma, vulvar cancer, skin cancer, endometrial cancer, ovarian cancer, prostate cancer, pancreatic cancer, colon cancer, rectum cancer, colorectal cancer, Kaposi's sarcoma, non-melanoma skin cancer (including squamous cell carcinoma and basal cell carcinoma), hemangioma, glioma and secondary complications of these diseases (such as pain, infection, pericardial effusion, and pleural effusion).

In some embodiments, the microorganism is selected from:

a bacterium (such as *Staphylococcus aureus, Escherichia coli, Pseudomonas aeruginosa, Shigella dysenteriae, Bacillus pertussis, Bacillus* diphtheria, Diplococcus *meningitidis, Mycobacterium tuberculosis, Clostridium tetani, Bacillus* leprosy, Group A hemolytic *streptococcus, Brucella, Bacillus* cholera, *Bacillus typhi, Bacillus anthracis, Neisseria gonorrhoeae, Propionibacterium acnes*, and *Salmonella* paratyphi A, B or C), a virus (such as influenza virus, mumps virus, rubella virus, encephalitis B virus, dengue virus, epidemic hemorrhagic fever virus, rabies virus, human papilloma virus, polio virus, measles virus, varicella-zoster virus, hepatitis virus, new enterovirus type 70, Coxsackie virus A24 variant, and human immunodeficiency virus), a fungus (such as *Candida albicans, Trichophyton rubrum*, and *Epidermophyton floccosum*), a *Mycoplasma* (such as *Mycoplasma pneumoniae, Ureaplasma urealyticum, Mycoplasma hominis*, and *Mycoplasma genitalium*), a *Chlamydia* (such as *Chlamydia trachomatis, Chlamydia pneumoniae, Chlamydia psittaci, Chlamydia* in livestock), a *Rickettsia* (such as *Rickettsia prowazekii, Rickettsia mooseri, Rickettsia ricketts*, and *Rickettsia tsutsugamushi*), an actinomycete (such as *Actinomyces* Israel), or a spirochete (such as *Leptospira* and *Treponema pallidum*).

In some embodiments, the parasite is selected from: roundworm, hookworm, tapeworm, *Trichomonas vaginalis*, liver fluke, *Paragonimus* Westmans, *Toxoplasma gondii*, Swine cysticercosis, Trichinella spiralis, Amoeba, *Leishmania donovani, Plasmodium*, Schistosome, Filaria, Hydatid, Scabies mite, hair follicle mite, lice, or flea.

In some embodiments, the disease related to microorganism or parasite infection is selected from extra-intestinal infection or diarrhea caused by *Escherichia coli*, viral hepatitis, bacterial and amoebic dysentery, gonorrhea, syphilis, polio, Measles, pertussis, diphtheria, epidemic cerebrospinal meningitis, scarlet fever, epidemic hemorrhagic fever, rabies, leptospirosis, brucellosis, anthrax, epidemic encephalitis B, kala-azar, malaria, dengue fever, tuberculosis, Schistosomiasis, filariasis, echinococcosis, leprosy, influenza, mumps, rubella, neonatal tetanus, acute hemorrhagic conjunctivitis, cholera, typhoid fever caused by typhoid bacilli, paratyphoid fever, *Mycoplasma* pneumonia, non-gonococcal urethritis, *Mycoplasma* cervicitis, trachoma, psittacosis, *Chlamydia* pneumonia, epidemic typhus, endemic typhus, Rocky Mountain spotted fever, Rickettsialpox, Tsutsugamushi, spotted fever, trench fever, ringworm (such as tinea versicolor, black tinea palm, nodose trichomycosis, tinea pedis, tinea hand, tinea corporis, tinea cruris, onychomycosis, and tinea capitis), Sporothriosis, Chromoblastomycosis, Candidiasis, Aspergillosis, Cryptococcosis, Zygomycosis, *Penicillium marneffei*, Condyloma Acuminatum, Herpes Zoster, AIDS, Pulmonary actinomycosis, acne, and other infectious diarrheal diseases.

In some embodiments, the immune-related disease is selected from:

secondary immunodeficiency, such infections (such as rubella, measles, leprosy, tuberculosis, cytomegalovirus infection, HIV infection, and coccidioidomycosis), protein loss (such as nephrotic syndrome and protein-losing enteropathy), insufficient immunoglobulin synthesis, lymphocyte loss (such as lymphocyte loss caused by drugs and/or systemic infection), other diseases (such as diabetes, cirrhosis, and subacute sclerosing panencephalitis) and/or secondary immunodeficiency caused by immunosuppressive therapy; and autoimmune diseases, such as systemic lupus erythematosus, rheumatoid arthritis, scleroderma, hyperthyroidism, juvenile diabetes, primary platelet purpura, autoimmune hemolytic anemia, ulcerative colitis, skin disease, and chronic liver disease.

Further, the compound, the pharmaceutically acceptable salt or ester, prodrug, stereoisomer, hydrate, solvate or crystal form of the compound, metabolite of each of them, or any combination or mixture thereof selected in the disclosure may be used for treating or diagnosing a precancerous lesion or a skin disease of a subject, or for skin beauty.

In some embodiments, the precancerous lesion is selected from cervical cancer precancerous lesions caused by papillomavirus infection and precancerous lesions of the following cancers: breast cancer, melanoma, meningioma, soft tissue sarcoma, salivary gland tumor, primary liver cancer, intraspinal tumor, mediastinal tumor, brain cancer, bone cancer, penile cancer, osteosarcoma, intracranial tumor, tongue cancer, maxillary sinus cancer, thyroid cancer, malignant lymphoma, multiple myeloma, pituitary adenoma, testicular tumor, non-Hodgkin's lymphoma, bladder cancer, leukemia, gastric cancer, nasopharyngeal cancer, laryngeal cancer, oral cancer, esophageal cancer, lung cancer, kidney cancer, choriocarcinoma, vulvar cancer, skin cancer, endometrial cancer, ovarian cancer, prostate cancer, pancreatic cancer, colon cancer, rectum cancer, colorectal cancer, Kaposi's sarcoma, non-melanoma skin cancer (including squamous cell carcinoma and basal cell carcinoma), hemangioma, and glioma.

In some embodiments, the skin disease is selected from condyloma acuminatum, acne related to microorganism infection, port wine stains, solar keratosis, skin cancer, precancerous lesions of skin cancer, and benign proliferative diseases of skin.

In some embodiments, the skin beauty includes: removal of pigmented skin lesions (such as melasma, freckles, etc.), exfoliating, and relief of acne associated with microorganism infection.

The compound, the pharmaceutically acceptable salt or ester, prodrug, stereoisomer, hydrate, solvate or crystal form of the compound, metabolite of each of them, or any combination or mixture thereof selected in the disclosure may be made into any pharmaceutically acceptable preparation, such as transdermal preparations (such as ointments, plasters, patches, paints, aerosols, gels, etc.), drops, perfusions, injections (such as liquid injections, injection powders or injection tablets), oral preparations (for example, oral solid preparations, such as tablets, capsules, pills, granules, etc.; or, oral liquid preparations, such as oral solutions, oral suspensions, syrups, etc.).

Further, compound, the pharmaceutically acceptable salt or ester, prodrug, stereoisomer, hydrate, solvate or crystal form of the compound, metabolite of each of them, or any combination or mixture thereof selected in the disclosure may be made into any preparation suitable for application to a surface of skin, such as creams, ointments, lotions, gels and the like.

In some embodiments, the preparation includes one or more pharmaceutically acceptable adjuvants (e.g., matrices, excipients, carriers, stabilizers, or solubilizers). Pharmaceutically acceptable carriers that can be used include, but are not limited to, sterile liquids, such as water and oils, including those of petroleum, animal, vegetable, or synthetic origin, such as peanut oil, soybean oil, mineral oil, sesame oil, and the like. When the preparation is administered by injection, water is used an exemplary carrier. Physiological saline, glucose or glycerol aqueous solution may also be used as a liquid carrier, especially for injection. Suitable pharmaceutical excipients include starch, glucose, lactose, sucrose, gelatin, maltose, chalk, silica gel, sodium stearate, glyceryl monostearate, talc, sodium chloride, skimmed milk powder, glycerin, propylene glycol, water, ethanol, and the like. The combination may also include a small amount of a wetting agent, an emulsifier or a pH buffer agent as needed. The oral preparations may include standard carriers, such as pharmaceutical-grade mannitol, lactose, starch, magnesium stearate, sodium saccharin, cellulose, magnesium carbonate and the like. Examples of suitable pharmaceutically acceptable carriers are described in Remington's Pharmaceutical Sciences (1990). The gel may use a natural, semi-synthetic or synthetic polymer material as the matrix, such as alginate, gelatin, pectin, cellulose derivatives, starch and its derivatives, povidone, polyvinyl alcohol, and polyacrylic acid (Carbomer, polyacrylic acid, etc.).

In some embodiments, the adjuvant is water or physiological saline.

According to another aspect, the disclosure further relates to a method for inhibiting activity of a tumor cell, microorganism or parasite, the method comprising:

step i: applying the compound, the pharmaceutically acceptable salt or ester, prodrug, stereoisomer, hydrate, solvate or crystal form of the compound, metabolite of each of them, or any combination or mixture thereof according to any of the above to the tumor cell, microorganism or parasite; and step ii: irradiating the tumor cell, microorganism or parasite with light.

In step ii, a single-wavelength light or a mixed light may be used.

In some embodiments, in step ii, at least part of the wavelength of the light is in a range of 10 nm to 1 mm, for example, in one or more of a range of 10 nm to 380 nm, a range of 380 nm to 780 nm, a range of 780 nm to 3 m, a range of 3 μm to 30 μm, and a range of 30 μm to 1 mm. In some embodiments, at least part of the wavelength of the light is in a range of 400 nm to 480 nm. In some embodiments, at least part of the wavelength of the light is in a range of 450 nm to 480 nm.

In some embodiments, in step ii, the irradiation is carried out for 1 s to 12 h, for example, 1 s to 10 s, 10 s to 100 s, 100 s to 200 s, 200 s to 500 s, or 500 s to 900 s, for example, 1 min to 10 min, 10 min to 30 min, or 30 min to 60 min, for example, 1 h to 2 h, 2 h to 5 h, or 5 h to 12 h.

In some embodiments, in step ii, the irradiation is carried out at a light intensity of 1-2000 $mW/cm^2$, (e.g., 1 to 15 $mW/cm^2$, 15 $mW/cm^2$ to 50 $mW/cm^2$, 50 $mW/cm^2$ to 100 $mW/cm^2$, 100 $mW/cm^2$ to 200 $mW/cm^2$, 200 $mW/cm^2$ to 300 $mW/cm^2$, 300 $mW/cm^2$ to 500 $mW/cm^2$, 500 $mW/cm^2$ to 1000 $mW/cm^2$, 1000 $mW/cm^2$ to 1500 $mW/cm^2$, or 1500 $mW/cm^2$ to 2000 $mW/cm^2$.

The method can be performed in a subject in vivo or in vitro, and can be used for therapeutic or non-therapeutic purposes. In some embodiments, the method is used for non-therapeutic purposes and is performed in vitro. For example, the method can be used for inhibiting the activity of a microorganism or parasite on the surface of human or an animal (excluding wounds and infected parts) or on the surface of an object; or, the method can be used in in vitro experiments for research purposes.

In some embodiments, the tumor cell is selected from breast cancer cell, melanoma cell, meningioma cell, soft tissue sarcoma cell, salivary gland tumor cell, primary liver cancer cell, intraspinal tumor cell, mediastinal tumor cell, brain cancer cell, bone cancer cell, penile cancer cell, osteosarcoma cell, intracranial tumor cell, tongue cancer cell, maxillary sinus cancer cell, thyroid cancer cell, malignant lymphoma cell, multiple myeloma cell, pituitary adenoma cell, testicular tumor cell, non-Hodgkin's lymphoma cell, bladder cancer cell, leukemia cell, gastric cancer cell, nasopharyngeal cancer cell, laryngeal cancer cell, oral cancer cell, esophageal cancer cell, lung cancer cell, kidney cancer cell, cervical cancer cell, choriocarcinoma cell, vulvar cancer cell, skin cancer cell, endometrial cancer cell, ovarian cancer cell, prostate cancer cell, pancreatic cancer cell, colon cancer cell, rectal cancer cell, colorectal cancer cell, Kaposi's sarcoma cell, non-melanoma skin cancer (including squamous cell carcinoma and basal cell carcinoma) cell, hemangioma cell, or glioma cell.

In some embodiments, the microorganism is selected from:

a bacterium (such as *Staphylococcus aureus, Escherichia coli, Pseudomonas aeruginosa, Shigella dysenteriae, Bacillus pertussis, Bacillus* diphtheria, Diplococcus *meningitidis, Mycobacterium tuberculosis, Clostridium tetani, Bacillus* leprosy, Group A hemolytic *streptococcus, Brucella, Bacillus* cholera, *Bacillus typhi, Bacillus anthracis, Neisseria gonorrhoeae, Propionibacterium acnes*, and *Salmonella* paratyphi A, B or C), a virus (such as influenza virus, mumps virus, rubella virus, encephalitis B virus, dengue virus, epidemic hemorrhagic fever virus, rabies virus, human papilloma virus, polio virus, measles virus, varicella-zoster virus, hepatitis virus, new enterovirus type 70, Coxsackie virus A24 variant, and human immunodeficiency virus), a fungus (such as *Candida albicans, Trichophyton rubrum*, and *Epidermophyton floccosum*), a *Mycoplasma* (such as *Mycoplasma pneumoniae, Ureaplasma urealyticum, Mycoplasma hominis*, and *Mycoplasma genitalium*), a *Chlamydia* (such as *Chlamydia trachomatis, Chlamydia pneumoniae, Chlamydia psittaci, Chlamydia* in livestock), a *Rickettsia* (such as *Rickettsia prowazekii, Rickettsia mooseri, Rickettsia ricketts*, and *Rickettsia tsutsugamushi*), an actinomycete (such as *Actinomyces* Israel), or a spirochete (such as *Leptospira* and *Treponema pallidum*).

In some embodiments, the parasite is selected from: roundworm, hookworm, tapeworm, *Trichomonas vaginalis*, liver fluke, *Paragonimus* Westmans, *Toxoplasma gondii*, Swine cysticercosis, Trichinella spiralis, Amoeba, *Leishmania donovani, Plasmodium*, Schistosome, Filaria, Hydatid, Scabies mite, hair follicle mite, lice, or flea.

In the disclosure, the subject is preferably a mammal, such as a bovine, equine, swine, canine, feline, rodent, or primate, for example, human.

Definition of Terms

In the disclosure, the term "photodynamic therapy" refers to a photochemotherapy, which is based on sensitization with a photosensitizer to induce oxygen to produce reactive oxygen species (ROS) represented by singlet oxygen, which can kill tumor cells, pathogenic microorganisms or the like to achieve the purpose of treating diseases. The photodynamic therapy can also be used for skin beauty, such as removing wrinkles, removing sagging skin, removing pigmented skin lesions, removing skin hyperplasia, and removing keratin, and the like.

In the disclosure, the term "photodynamic diagnosis" refers to a photochemical diagnosis method that uses the characteristic spectrum of a photosensitizer that has an affinity to tumors or other diseased tissues to diagnose diseases under the action of light.

In the disclosure, the term "single-wavelength light" refers to light of which a half-value width of the peak of the spectral intensity distribution is 10 nm or less.

In the disclosure, the term "mixed light" refers to light obtained by mixing a plurality of single-wavelength lights.

In the disclosure, the term "photosensitizer" refers to a chemical substance that absorbs energy of a light with a specific wavelength and transfers the energy to other molecules, thereby generating active oxygen and other substances that can kill cells or microorganisms.

In the disclosure, the term "microorganism" includes bacteria, viruses, fungi, and some small protists, microalgae and other tiny organisms that are difficult to observe with the naked eye. The microorganisms that cause diseases in humans or animals are called pathogenic microorganisms, which usually include fungi, actinomycetes, spirochetes, bacteria, *Rickettsia, Chlamydia*, viruses, and mycoplasmas.

The disclosure has the following beneficial effects.

The organic small-molecule diketone photosensitizer used in the disclosure has weak intermolecular aggregation effect, low toxicity, and good water solubility, still maintains good photochemical properties in a water phase, and is cheap and easily available. The diketone compound used in the disclosure achieves at least one of the following technical effects under light excitation:

(1) inhibiting the activity of tumor cells;
(2) inhibiting the activity of bacteria and other microorganisms;
(3) enhancing immunity;
(4) good bioavailability; and
(5) good safety.

The disclosure can be used to treat a tumor or a disease caused by microorganism or parasitic infection, can be used to enhance immunity, and can also be used for skin beauty, thus having an important clinical value.

The embodiments of the disclosure will be described in detail below in conjunction with the drawings and examples. However, those skilled in the art will understand that the following drawings and examples are only used to illustrate the disclosure, not to limit the scope of the disclosure. Various objectives and advantageous aspects of the disclosure will become apparent to those skilled in the art based on the drawings and the following detailed description of the preferred embodiments.

DETAILED DESCRIPTION

Figure 1:
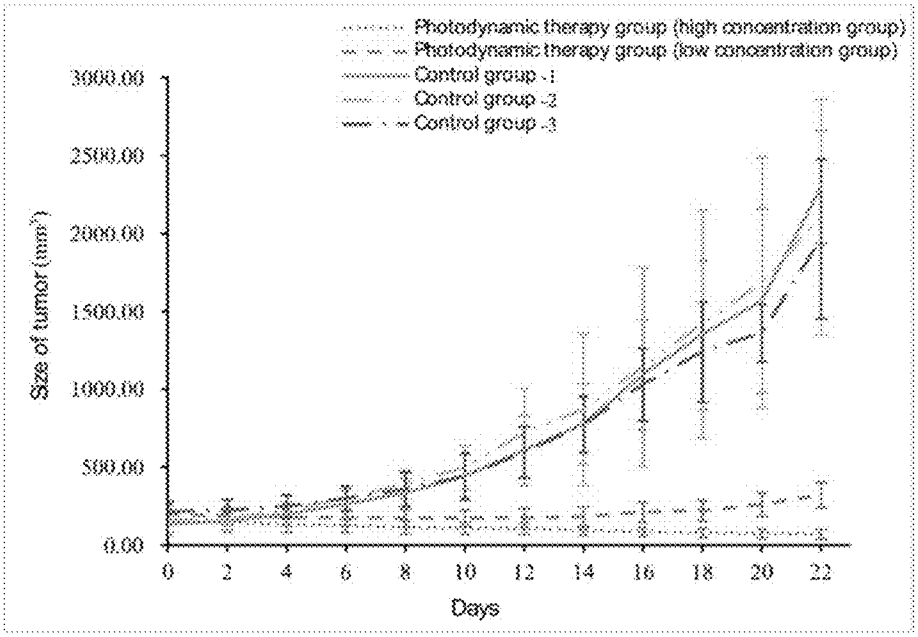
FIG. 1 shows size changes of tumor tissues in BALB/C mice during 2 weeks of treatment in Experimental Example 3. As shown in the figure, 14 days after administration, there is a very significant difference between a high-concentration treated group and a control group ($p<0.001$), and there is also a very significant difference between a low-concentration treated group and the control group ($p<0.001$). The tumor size is controlled and decreased, and this effect is more prominent in the high-concentration treated group. This experiment shows that the diketone compound has an inhibitory effect on the tumor.

The embodiments of the disclosure will be described in detail below in conjunction with examples. However, those skilled in the art will understand that the following examples are only used to illustrate the disclosure, not to limit the scope of the disclosure. Those without specific conditions in the examples are generally implemented under conventional conditions or conditions recommended by the manufacturers. The reagents or instruments used without specifying the manufacturers are all conventional products that can be purchased commercially.

Bioactivity Experiment

Cells, reagents, and instruments involved in in vitro experiments in the following experimental examples are as follows:

Drugs:

Compounds BJMU-201 to BJMU-214, all purchased from companies such as J&K Scientific Ltd., Beijing Ouhe Technology Co. Ltd., or Beijing InnoChem Science & Technology Co., Ltd.

Cells:

SW480 colon cancer cells, Hela cells, and B16 melanoma cell, all provided by the ATCC cell bank.

Culture Solutions:

RPMI 1640 medium and fetal bovine serum (FBS); DMEM (containing 2 mL-glutamine and Earle's BSS, 1.5 g/L $NaHCO_3$, 0.1 mM non-essential amino acids, 1.0 mM sodium pyruvate) and FBS.

Cell Culture:

Under the environment conditions of 37° C., 5% $CO_2$ and saturated humidity, the cells were incubated to a confluence of 80%, and then digested with 0.25% trypsin-EDTA.

Main Reagents and Instruments Involved:

DMEM high-sugar medium, 1640 medium, and trypsin (Gibco, Maryland, USA); FBS (PAN, Germany); low-temperature refrigerated high-speed centrifuge (Beijing DLAB Scientific, China); horizontal shaker (ZD-9550, Kylin Bell Lab Instruments, Jiangsu); ultra-clean workbench (Suzhou Antai Airtech, Suzhou); FlexStation 3 multifunctional microplate reader (Molecular Devices).

Experimental Example 1 Evaluation of Compound's Toxicity to Tumor Cells

In this experimental example, the toxicity of the compound to tumor cells was tested by an MTT method including the following specific steps.

(1) Logarithmic cells were collected, the concentration of a cell suspension was adjusted, the cell suspension was added to a cell culture plate in a dose of 100 μL per well, and the cells were then added to a cell culture plate so that the density of the cells to be tested was adjusted to 1000-10000 wells (edge wells were filled with sterile PBS).

(2) The cells were incubated at 37° C. in the presence of 5% $CO_2$ until the cells in a single layer covered the bottom of each well (96-well flat-bottom plate), and a drug in concentration gradients was added. Generally, the drug in 5 to 7 gradients was added in a dose of 100 μL per well, and 3 to 5 multi-wells were set.

(3) The cells were randomly divided into treated groups under light and treated groups in the dark, incubated at 37° C. in the presence of 5% $CO_2$ for 16 h to 48 h, and observed with an inverted microscope.

(4) The cells were irradiated for 900 s with a laser having a wavelength of 450 nm to 480 nm (at an intensity of 110 mW/cm$^2$), and the final light dose was about 100 J/cm$^2$. After light irradiation, the cells were washed with PBS.

(5) An MTT solution (5 mg/ml, 0.5% MTT) was added in a dose of 20 μL per well to further incubate the cells for 4 h. If the drug could react with the MTT, centrifuging was carried out first, and then the culture solution was discarded and the cells were carefully washed twice or three times with PBS, and then the culture solution containing MTT was added.

(6) The culture was terminated and the culture solution in the wells was carefully removed.

(7) Dimethyl sulfoxide was added in a dose of 150 μL per well, and the plate was then shaken on a shaker at a low speed for 10 min to fully dissolve crystals. The absorbance at OD 490 nm of each well was measured with enzyme-linked immunoassay.

(8) Zero adjustment wells (medium, MTT, dimethyl sulfoxide) and control wells (cells, dissolving media of the same concentration, culture solution, MTT, dimethyl sulfoxide) were set at the same time.

Table 1-1 and Table 1-2 show the toxicity of 14 tested compounds (BJMU-201 to BJMU-214) to three tumor cells under light. The results show that the selected diketone compounds of the disclosure have relatively high cytotoxicity to the SW480 cells, Hela cells and B16 cells when given under light. The above results indicate that the compound of the disclosure has significant inhibitory activity to the tumor cells.

TABLE 1-1

Cytotoxicity of diketone compounds to different tumor cells under light

| | $IC_{50}$(μM) | | |
|---|---|---|---|
| Compound | SW480 | Hela | B16 |
| BJMU-201 | 63.9 ± 10.5 | 59.9 ± 9.9 | 64.4 ± 10.6 |
| BJMU-202 | 2.5 ± 0.5 | 2.6 ± 0.6 | 2.9 ± 0.1 |

TABLE 1-1-continued

Cytotoxicity of diketone compounds to different tumor cells under light

| | $IC_{50}$(μM) | | |
|---|---|---|---|
| Compound | SW480 | Hela | B16 |
| BJMU-203 | 3.1 ± 0.5 | 2.8 ± 1.1 | 2.7 ± 0.9 |
| BJMU-204 | 0.6 ± 0.05 | 0.6 ± 0.02 | 0.5 ± 0.03 |
| BJMU-205 | 6.4 ± 1.9 | 5.7 ± 1.7 | 6.6 ± 1.8 |
| BJMU-206 | 143.8 ± 31.9 | 141.1 ± 37.4 | 144.2 ± 32.5 |
| BJMU-207 | 99.2 ± 25.7 | 93.3 ± 20.3 | 96.6 ± 26.3 |
| BJMU-208 | 172.9 ± 10.8 | 162 ± 10.1 | 174.3 ± 10.9 |

TABLE 1-2

Cytotoxicity of diketone compounds to different tumor cells under light

| | $IC_{50}$(mM) | | |
|---|---|---|---|
| Compound | SW480 | Hela | B16 |
| BJMU-209 | 7.8 ± 0.48 | 8.2 ± 0.53 | 8.1 ± 0.45 |
| BJMU-210 | 9.6 ± 0.6 | 9.9 ± 0.7 | 9.8 ± 0.7 |
| BJMU-211 | 3.2 ± 0.23 | 3.8 ± 0.29 | 3.6 ± 0.26 |
| BJMU-212 | 2.8 ± 0.21 | 2.7 ± 0.17 | 3 ± 0.27 |
| BJMU-213 | 6.6 ± 0.37 | 6.4 ± 0.4 | 6.9 ± 0.41 |
| BJMU-214 | 8.9 ± 0.5 | 8.8 ± 0.48 | 9 ± 0.51 |

Table 2 shows the toxicity of 14 tested compounds (BJMU-201 to BJMU-214) to three tumor cells in the dark. The results show that the selected diketone compounds of the disclosure have relatively low cytotoxicity to the SW480 cells, Hela cells and B16 cells when given in the dark. The above results indicate that the compound of the disclosure has good safety.

TABLE 2

Cytotoxicity of diketone compounds to different tumor cells in the dark

| | $IC_{50}$(mM) | | |
|---|---|---|---|
| Compound | SW480 | Hela | B16 |
| BJMU-201 | 207.3 ± 55.6 | 194.2 ± 52.1 | 208.9 ± 56 |
| BJMU-202 | 246.7 ± 12.2 | 205.7 ± 11.4 | 251.7 ± 12.3 |
| BJMU-203 | 131.4 ± 5.5 | 197.7 ± 5.2 | 135.5 ± 5.6 |
| BJMU-204 | 263.9 ± 39.6 | 253.5 ± 37.1 | 265.2 ± 39.9 |
| BJMU-205 | 371.2 ± 29 | 360.4 ± 27.2 | 372.5 ± 29.3 |
| BJMU-206 | 172.9 ± 10.8 | 162 ± 10.1 | 174.3 ± 10.9 |
| BJMU-207 | 113.8 ± 49.7 | 175 ± 46.5 | 118.6 ± 50 |
| BJMU-208 | 204.1 ± 73.5 | 253.2 ± 68.9 | 210.4 ± 74.1 |
| BJMU-209 | 138.3 ± 28.6 | 139 ± 29.1 | 143.8 ± 30.7 |
| BJMU-210 | 185.1 ± 42.1 | 179.9 ± 48.4 | 200.4 ± 50.2 |
| BJMU-211 | 95 ± 21.3 | 99 ± 19.8 | 99 ± 22.5 |
| BJMU-212 | 99 ± 15.8 | 98 ± 16.3 | 96 ± 14.9 |
| BJMU-213 | 136 ± 35.1 | 142 ± 37.2 | 139 ± 42.0 |
| BJMU-214 | 105 ± 23.8 | 109 ± 26.7 | 108 ± 25.2 |

Experimental Example 2 Evaluation of Compound's Inhibitory Effect on Bacteria A single *Escherichia coli* colony was transferred from a solid Luria Bertani (LB) agar plate to 5 ml liquid LB medium and incubated at 37° C. for 12 h. Bacteria were collected by centrifugation (7000 rpm, 1 min) and washed with PBS buffer three times. The supernatant was discarded, and the remaining *Escherichia coli* cells were resuspended in the PBS buffer. The bacterial suspension was adjusted to make its optical density (OD600) to 1.0. The suspension was then diluted (5 times) with PBS buffer. The diluted *Escherichia coli* cell suspension was incubated in the dark at 37° C. for 15 min in the presence of a photosensitizer (diketone compound) solution with a concentration of 60 mM, and then irradiated for 200 s under a 15 $mW/cm^2$ laser light (with a wavelength of 450 nm to 480 nm and in the final light dose of about 3 J $cm^2$), and after the irradiation the bacterial suspension was serially diluted ($10^4$ times) with PBS buffer. 100 μL of the diluted bacterial *Escherichia coli* cell was dispersed on a solid LB agar plate and incubated at 37° C. for 12 h to 16 h, and colonies formed were counted. In the meanwhile, a treated group in the dark and an untreated group in the dark were set; the inhibition rate was determined by dividing the number of colony forming units (cfu) killed in the treated group under light or the treated group in the dark by the number of colony forming units (cfu) killed in the untreated group in the dark.

The results are shown in Table 3. The diketone compounds have a significant inhibitory effect on the growth of *Escherichia coli* under light. The results indicate that the compound of the disclosure has significant antibacterial activity. The diketone compounds have a slight inhibitory effect on the growth of *Escherichia coli* in the dark. The results indicate that the compound of the disclosure has good safety.

TABLE 3

Inhibition rates of diketone compounds to *Escherichia coli* under light and in the dark

| Compound | Inhibition rate under light | Inhibition rate in the dark |
|---|---|---|
| BJMU-201 | 58% ± 7% | 4.9% ± 1% |
| BJMU-202 | 90 ± 3% | 8.6% ± 1.7% |
| BJMU-203 | 93% ± 9% | 4.5% ± 0.9% |
| BJMU-204 | 96% ± 1% | 10.3% ± 2.1% |
| BJMU-205 | 80% ± 2% | 2% ± 0.4% |
| BJMU-206 | 46% ± 5% | 11.5% ± 2.3% |
| BJMU-207 | 64% ± 4% | 7.3% ± 1.5% |
| BJMU-208 | 45% ± 7% | 8% ± 3% |
| BJMU-209 | 26% ± 3% | 9.5% ± 2.1% |
| BJMU-210 | 24% ± 4% | 6.4% ± 3.2% |
| BJMU-211 | 31% ± 2% | 7.2% ± 1.3% |
| BJMU-212 | 33% ± 7% | 3.6% ± 2.5% |
| BJMU-213 | 28 ± 5% | 6.1% ± 3.3% |
| BJMU-214 | 23% ± 3% | 5.6% ± 2.1% |

Experimental Example 3 Evaluation of Compound's Inhibitory Effect on Tumor (Animal Experiment)

1. Photodynamic therapy experiments on tumors were carried out by using BJMU-204 as a photosensitizer and BALB/C mice as experimental animals.

Modeling mode: BALB/C mice were divided into 5 groups in total, 11-12 mice in each group. 4T1 cells (breast cancer cells in mice) were resuscitated and subcultured to a better cell state for tumorigenesis inoculation. BALB/C mice were locally depilated and disinfected, and tumor cells were injected into the mouse mammary fat pad in situ. Tumors were formed within 7 to 10 days.

Administration time: drug intervention was given to mice after tumor formation, and photodynamic therapy was given by intratumoral injection every other day under the irradiation of laser with a wavelength of 450 nm to 480 nm at a light intensity of 200 $mW/cm^2$.

Administration mode: as shown in the table below, the photosensitizer was dissolved in physiological saline and injected in mice in groups 1-3 intratumorally, and the groups receiving photodynamic therapy were irradiated with light immediately after the injection.

| No. | Group | Mode of administration |
|---|---|---|
| Group 1 | Photodynamic therapy group (High-concentration group) | High-concentration (3%) intratumoral injection + light irradiation for 10 min at the tumor site |
| Group 2 | Photodynamic therapy group (Low-concentration group) | Low-concentration (0.5%) intratumoral injection + light irradiation for 10 min at the tumor site |
| Group 3 | Control group-1 | Intratumoral injection at a concentration of 3% |
| Group 4 | Control group-2 | Light irradiation for 10 min at the tumor site |
| Group 5 | Control group-3 | No administration, no light irradiation at the tumor site |

2. Mice in each experimental group were subjected to blood collection for serum separation and necropsy, and tumors were taken out and measured to obtain their wet weights; tumor tissues were fixed, pathological examinations were performed, and H. E. staining was used to observe the changes of tumors of the mice under an optical microscope; blood routine indicators (including white blood cell count (WBC), red blood cell count (RBC), lymphocyte count (LY), platelet count (PLT) and many other blood routine indicators) and blood biochemical indicators (including routine blood biochemical indicators) were tested and analyzed in the Laboratory of Peking University Third Hospital.
3. Tumors were taken out of mice in each experimental group, a piece of tumor tissue about 1 cm*1 cm*0.5 cm in size was cut up and placed in a 10 ml EP tube. 5 ml of pancreatin was added for digestion. 30 min later, the digestion was ended. The digestion solution and the tumor tissue were sieved through a single cell sieve to obtain a tumor tissue single-cell suspension. B220 antibody (for flow cytometry) was added to the suspension and the resulting solution was stained with a PI staining solution; 30 min later, the staining was ended and the staining solution was removed; next, re-suspending was carried out with a PBS solution for test with a flow cytometry.

FIG. 1 shows size changes of tumor tissues in BALB/C mice during 2 weeks of treatment. As shown in the figure, 14 days after treatment, there is a very significant difference between a high-concentration treated group and a control group ($p<0.001$), and there is also a very significant difference between a low-concentration treated group and the control group ($p<0.001$). The tumor size is controlled and decreased, and this effect is more prominent in the high-concentration treated group. This experiment shows that the diketone compound has an inhibitory effect on the tumor.

Figure 2:
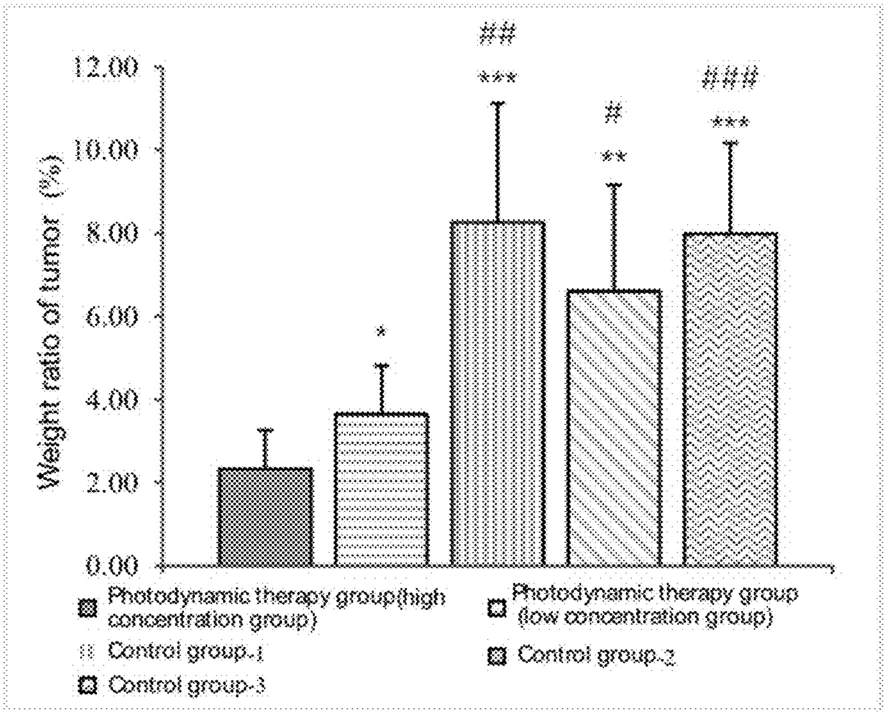
FIG. 2 shows weight changes of tumor tissues in BALB/C mice after 2 weeks of treatment in Experimental Example 3. As shown in the figure, 14 days after administration of the diketone compound, there is a very significant difference between a high-concentration treated group and a control group ($p<0.001$), and there is also a very significant difference between a low-concentration treated group and the control group ($p<0.001$). Based on weight ratios of tumors, an obvious growth inhibition effect is shown in the treated groups and a better inhibitory effect on the tumor is shown in the high-concentration treated group. This experiment shows that the diketone compound has an inhibitory effect on the tumor.

FIG. 2 shows weight changes of tumor tissues in BALB/C mice after 2 weeks of treatment. As shown in the figure, 14 days after treatment, there is a very significant difference between a high-concentration treated group and a control group ($p<0.001$), and there is also a very significant difference between a low-concentration treated group and the control group ($p<0.001$). Based on weight ratios of tumors, an obvious growth inhibition effect is shown in the treated groups and a better inhibitory effect on the tumor is shown in the high-concentration treated group. This experiment shows that the diketone compound has an inhibitory effect on the tumor.

Figure 3:
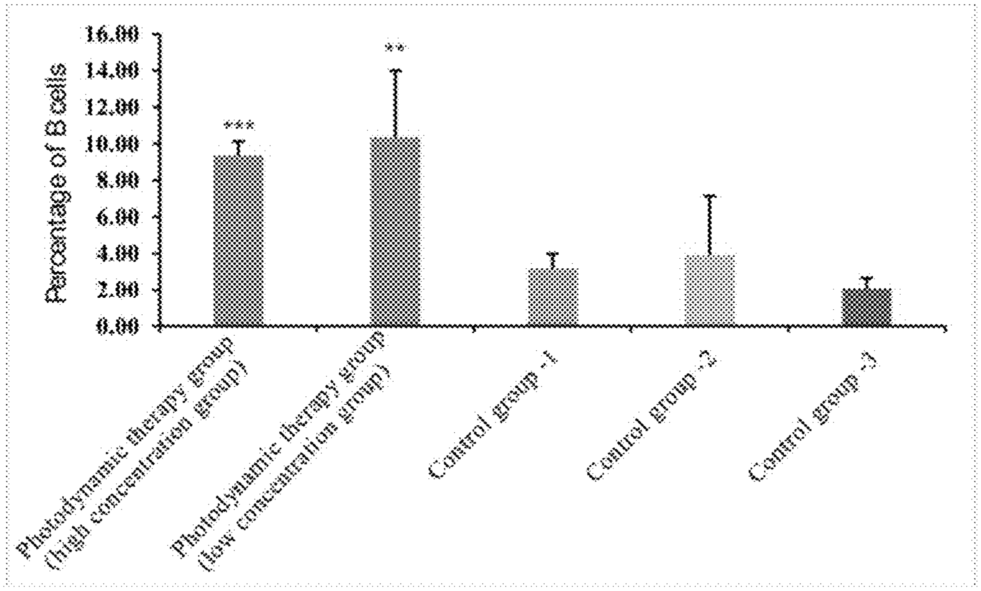
FIG. 3 shows the number of B cells in tumor tissues of BALB/C mice after 2 weeks of treatment in Experimental Example 3. As shown in the figure, 14 days after administration of the diketone compound, there is a very significant difference between a high-concentration treated group and a control group ($p<0.001$), and there is also a very significant difference between a low-concentration treated group and the control group ($p<0.01$). The number of B cells in tumor tissues in the treated groups increases significantly, and a better immune enhancement effect is shown in the high-concentration treated group.

FIG. 3 shows the number of B cells in tumor tissues of BALB/C mice after 2 weeks of treatment. As shown in the figure, 14 days after treatment, there is a very significant difference between a high-concentration treated group and a control group ($p<0.001$), and there is also a very significant difference between a low-concentration treated group and the control group ($p<0.01$). The number of B cells in tumor tissues in the treated groups increases significantly, and a better immune enhancement effect is shown in the high-concentration treated group.

Table 4 shows the results of blood routine tests of BALB/C mice after 2 weeks of treatment. The number of platelets and white blood cells in the blood of mice decreases, and there is a very significant difference between the treated groups and the control groups ($p<0.001$). The number of platelets and white blood cells decreases in the treated groups, indicating that the immune function in the treated groups is enhanced. This experiment shows that photodynamic therapy involving the diketone compounds enhance immunity.

Figure 4:
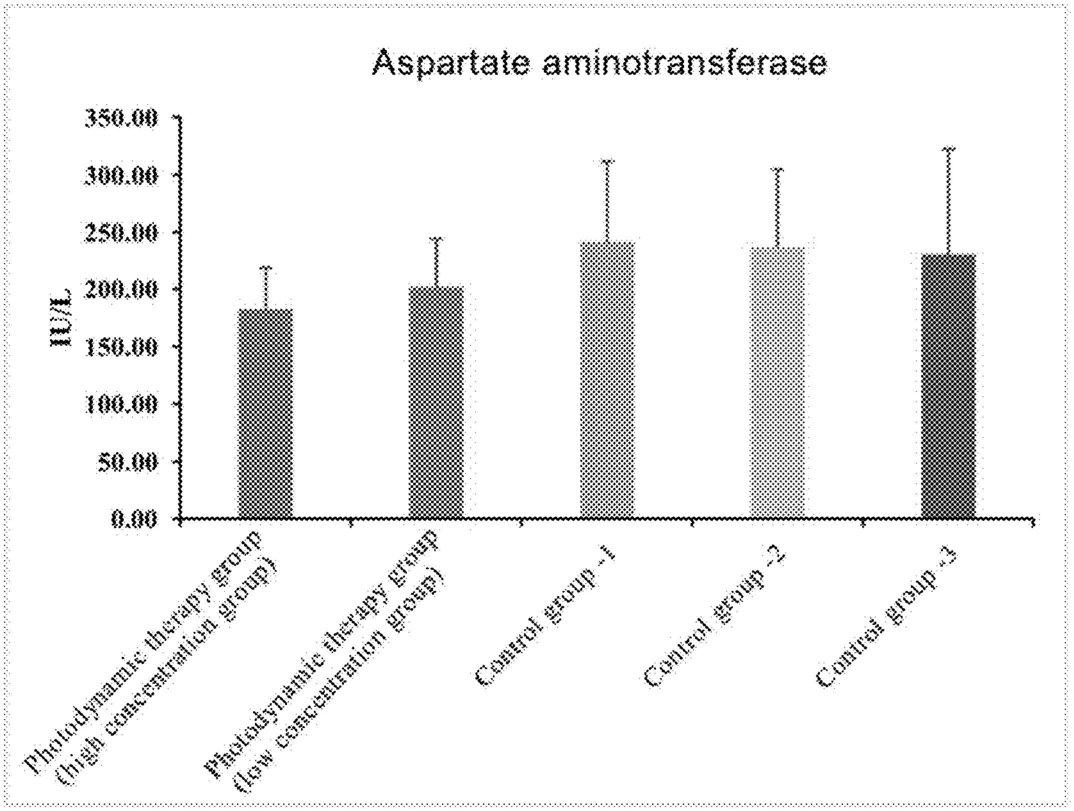
FIG. 4 shows the level of aspartate aminotransferase in blood of BALB/C mice after 2 weeks of treatment in Experimental Example 3.
Figure 5:
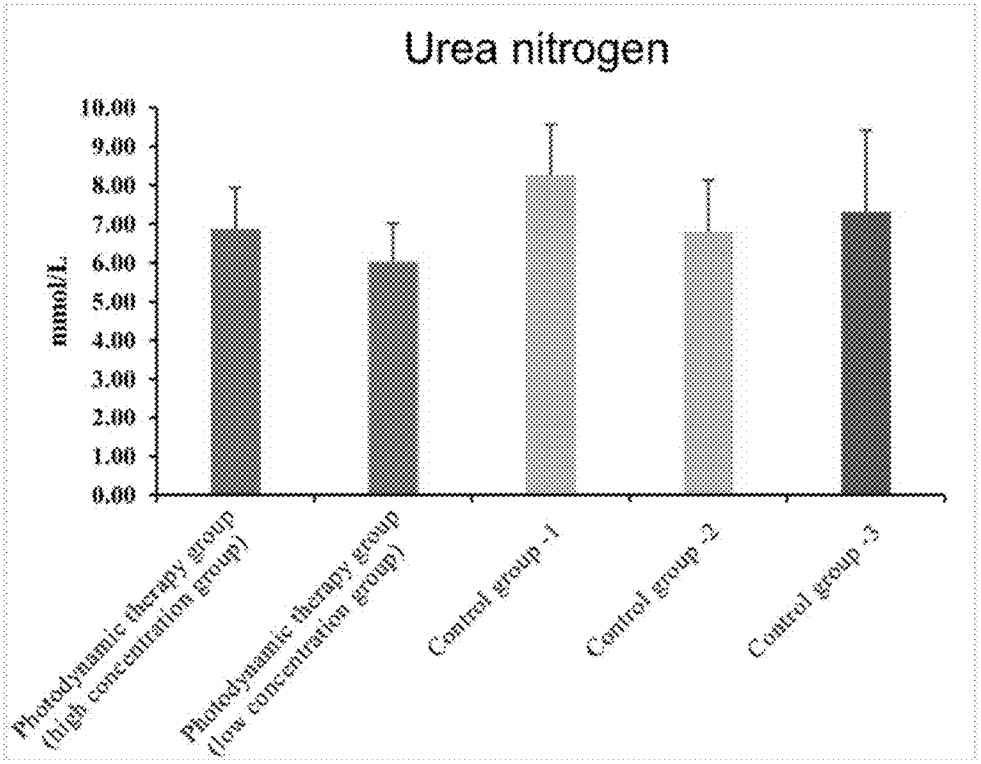
FIG. 5 shows the level of urea nitrogen in blood of BALB/C mice after 2 weeks of treatment in Experimental Example 3.
Figure 6:
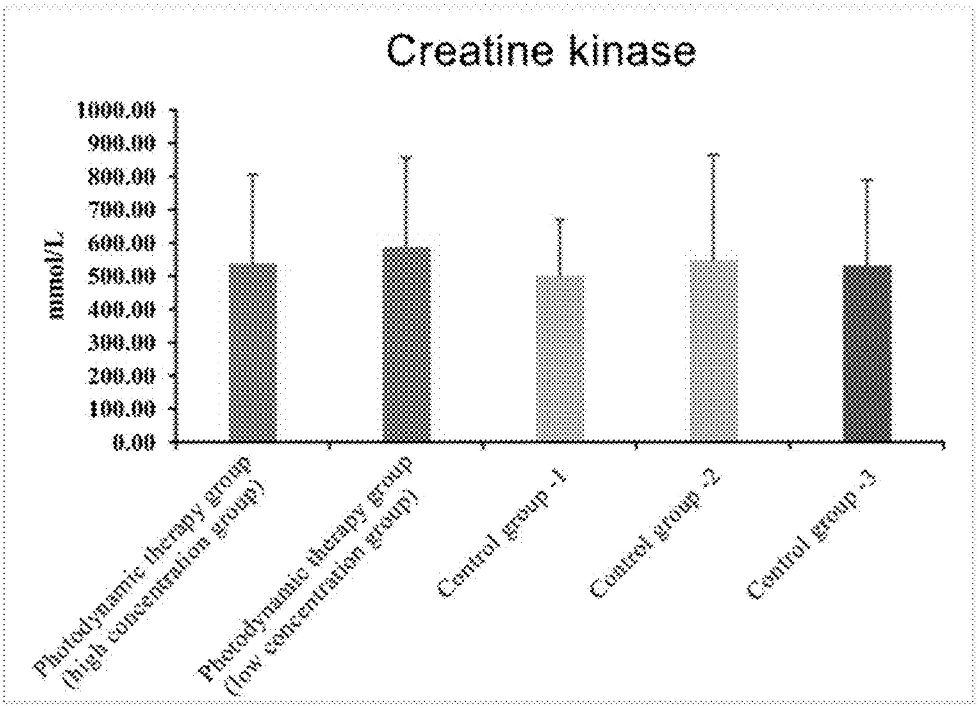
FIG. 6 shows the level of creatine kinase in the blood of BALB/C mice after 2 weeks of treatment in Experimental Example 3.

FIG. 4 to FIG. 6 show the blood biochemical data of BALB/C mice after 2 weeks of treatment. FIG. 4, FIG. 5, and FIG. 6 respectively correspond to the levels of aspartate aminotransferase, urea nitrogen, and creatine kinase.

The blood routine data (except LY and PLT) of BALB/C mice in Table 4 and the blood biochemical data in FIG. 4 to FIG. 6 show that diketone compounds will not cause liver, kidney and blood toxicity after continuous treatment for 14 days at high or low concentration therapeutic doses.

TABLE 4

12 h mouse blood routine results of mice after 2 weeks of treatment in BALB/C mice

| | Photodynamic therapy group (High-concentration group) | Photodynamic therapy group (Low-concentration group) | Control group-1 | Control group-2 | Control group-3 |
|---|---|---|---|---|---|
| Hematocrit (HCT) | 32.4 ± 12.48 | 32.64 ± 12.12 | 28.8 ± 5.76 | 28.44 ± 5.88 | 27.6 ± 1.68 |
| Hemoglobin (HGB) | 123 ± 40.8 | 141.6 ± 42.72 | 117 ± 26.64 | 132 ± 16.92 | 132 ± 0 |
| Mean corpuscular hemoglobin (MCH) | 18.43 ± 1.93 | 20.1 ± 1.84 | 18.43 ± 0.67 | 21.47 ± 2.2 | 22.1 ± 1.84 |
| Mean corpuscular hemoglobin concentration (MCHC) | 387.5 ± 40.38 | 447 ± 48.54 | 404.5 ± 26.01 | 456.5 ± 32.02 | 479 ± 29.7 |
| Mean corpuscular volume (MCV) | 47.5 ± 1.95 | 45.04 ± 1.21 | 45.65 ± 1.35 | 45.57 ± 1.75 | 46.05 ± 1.06 |
| Mean platelet volume (MPV) | 6.63 ± 0.76 | 6.23 ± 0.61 | 6.1 ± 0 | 6.55 ± 0.51 | 6.3 ± 0 |
| Plateletocrit (PCT) | 0.24 ± 0.12 | 0.48 ± 0.24 | 0.24 ± 0 | 0.6 ± 0.24 | 0.36 ± 0 |
| Platelet distribution width (PDW) | 15.13 ± 0.76 | 13.37 ± 1.47 | 16.2 ± 0 | 14.58 ± 0.99 | 14.2 ± 0 |
| Platelet count (PLT) | 267 ± 167.28 | 494.4 ± 387.6 | 312 ± 125.04 | 766.32 ± 340.56 | 360 ± 339.36 |
| Red blood count (RBC) | 6.81 ± 2.51 | 7.22 ± 2.62 | 6.33 ± 1.36 | 6.24 ± 1.24 | 6 ± 0.51 |
| Red blood cell volume distribution width (RDW) | 14.58 ± 0.84 | 13.78 ± 0.59 | 14.18 ± 0.75 | 14.06 ± 0.91 | 13.95 ± 0.07 |
| White blood cell count (WBC) | 136.8 ± 31.45 | 193.5 ± 70 | 352.8 ± 45.95 | 370.2 ± 133.97 | 472.2 ± 138.31 |

Experimental Example 4 Evaluation of Compound's Phototoxicity to Healthy Mice (Animal Experiment)

1. Phototoxicity Evaluation Experiments were Carried Out by Using BJMU-204 as a Photosensitizer and BALB/C Mice as Experimental Animals.

BALB/C mice were divided into 2 groups in total, 9 mice in each group. The mice were fed adaptively for 2 days. Mice in a control group were fed normally, and mice in an experimental group were given photodynamic therapy by subcutaneous injection every other day under the irradiation of laser with a wavelength of 450 nm to 480 nm at a light intensity of 200 $mW/cm^2$.

Administration mode: as shown in the table below, the photosensitizer was dissolved in physiological saline and subcutaneously injected in mice in the experimental group, and the group receiving photodynamic therapy was irradiated with light immediately after the injection.

| No. | Mode of administration |
|---|---|
| Experimental group | High-concentration (3%) subcutaneous injection + light irradiation for 10 min |
| Control group | Normal feeding |

2. The mice in the experimental group and the control group were weighed every other day. At the end of the experiment, the mice were subjected to blood collection for serum separation and necropsy, and blood routine indicators (including WBC, RBC, LY, PLT and many other blood routine indicators) and blood biochemical indicators (including routine blood biochemical indicators) were tested and analyzed in the Laboratory of Peking University Third Hospital.

Table 5 shows the blood routine data of BALB/C mice.

TABLE 5

12 h mouse blood routine results of mice after 2 weeks of treatment for BALB/C mice

| | Control group | Experimental group |
|---|---|---|
| Hematocrit (HCT) | 55.88 ± 16.52 | 45.22 ± 2.83 |
| Hemoglobin (HGB) | 187.63 ± 42.41 | 160.22 ± 12.07 |

TABLE 5-continued 12 h mouse blood routine results of mice after 2 weeks of treatment for BALB/C mice

| | Control group | Experimental group |
|---|---|---|
| Mean corpuscular hemoglobin (MCH) | 16.73 ± 0.56 | 16.18 ± 0.34 |
| Mean corpuscular hemoglobin concentration (MCHC) | 363.13 ± 12.52 | 354.11 ± 8.19 |
| Mean corpuscular volume (MCV) | 46.07 ± 0.53 | 45.71 ± 0.6 |
| Mean platelet volume (MPV) | 6.33 ± 0.49 | 6.23 ± 0.37 |
| Plateletocrit (PCT) | 0.21 ± 0.08 | 0.17 ± 0.03 |

TABLE 5-continued 12 h mouse blood routine results of mice after 2 weeks of treatment for BALB/C mice

| | Control group | Experimental group |
|---|---|---|
| Platelet distribution width (PDW) | 14.3 ± 0.91 | 14.84 ± 0.6 |
| Platelet count (PLT) | 321.50 ± 124.76 | 290 ± 50.23 |
| Red blood count (RBC) | 10.52 ± 1.45 | 9.9 ± 0.72 |
| Red blood cell volume distribution width (RDW) | 13.16 ± 1.33 | 12.67 ± 0.54 |
| White blood cell count (WBC) | 7.03 ± 1.45 | 6.56 ± 0.54 |

Figure 7:
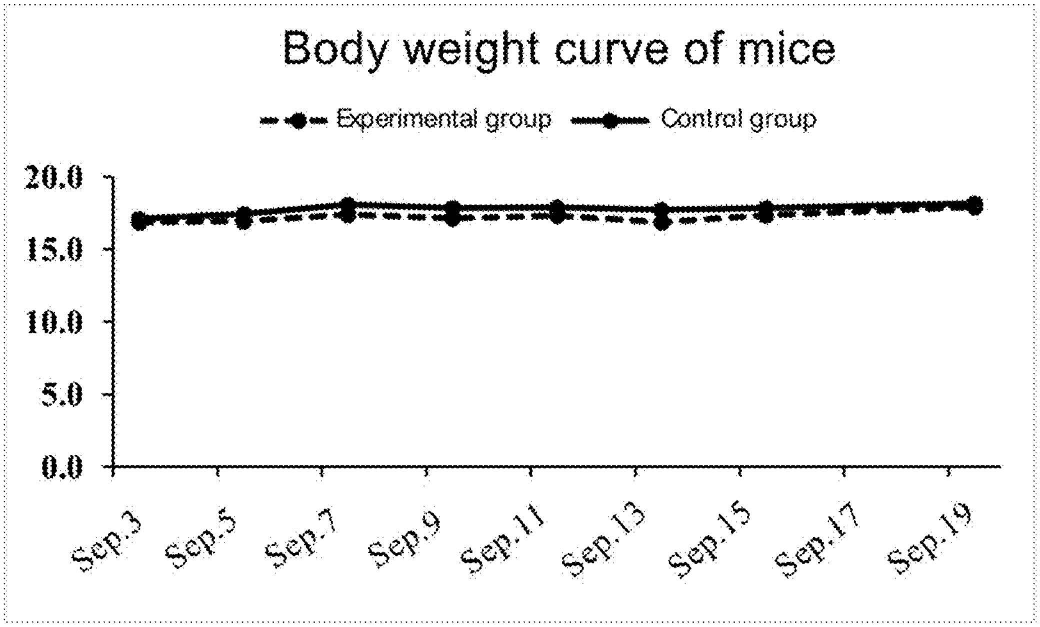
FIG. 7 shows changes in body weights of BALB/C mice during 2 weeks of treatment in Experimental Example 4.

FIG. 7 shows changes of body weight of BALB/C mice during 2 weeks of treatment. As shown in the figure, 14 days after treatment, there is no significant difference in body weight between the control group and the experimental group ($p<0.05$), and there is no significant change in the body weight of the experimental group during the treatment period. This experiment shows that the diketone compound has little phototoxicity to normal mice.

Figure 8:
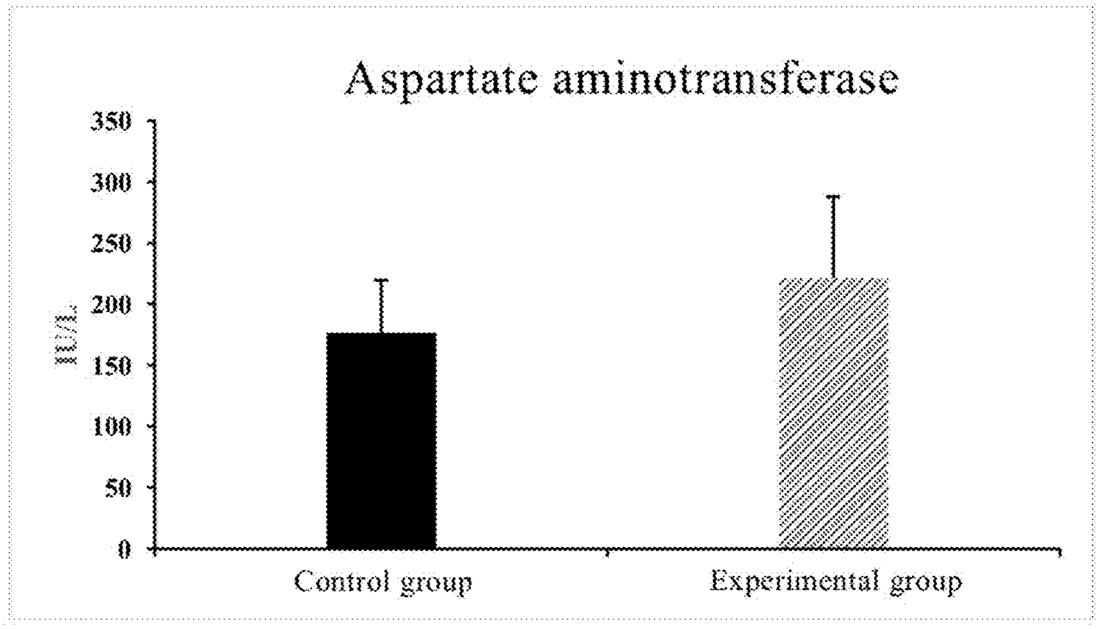
FIG. 8 shows the level of aspartate aminotransferase in blood of BALB/C mice after 2 weeks of treatment in Experimental Example 4.
Figure 9:
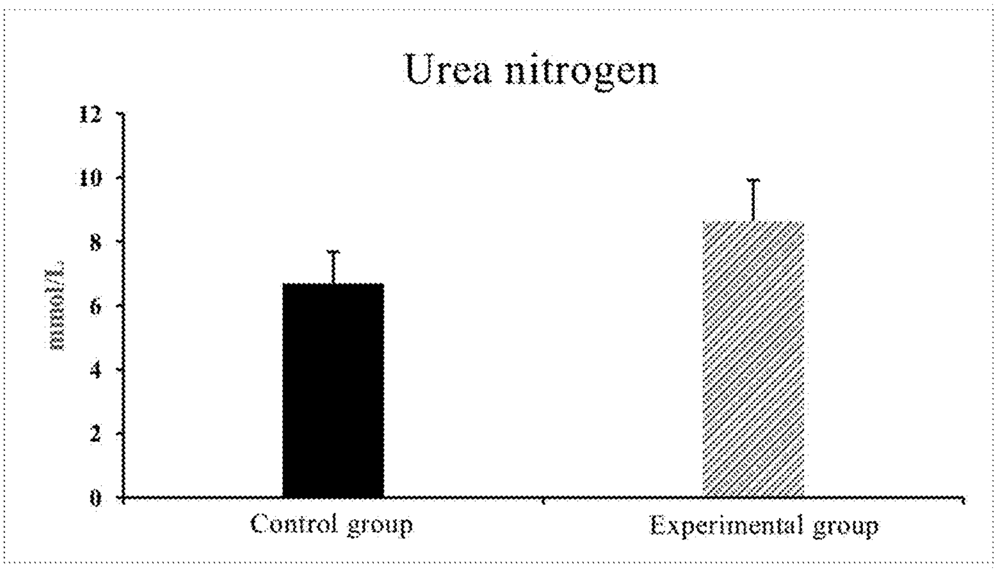
FIG. 9 shows the level of urea nitrogen in blood of BALB/C mice after 2 weeks of treatment in Experimental Example 4.
Figure 10:
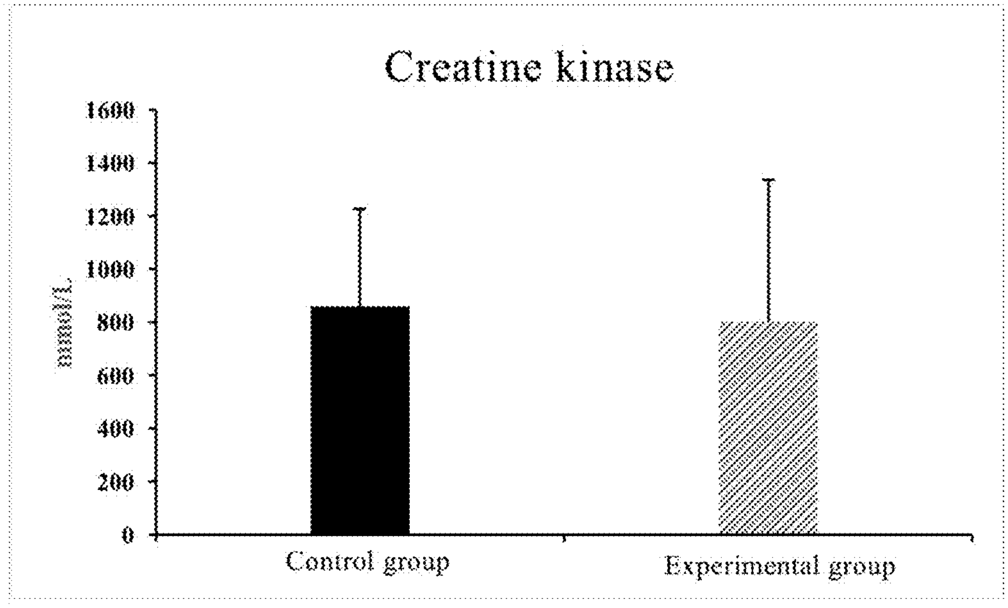
FIG. 10 shows the level of creatine kinase in the blood of BALB/C mice after 2 weeks of treatment in Experimental Example 4.

FIG. 8 to FIG. 10 show the blood biochemical data of BALB/C mice after 2 weeks of treatment. FIG. 8, FIG. 9, and FIG. 10 respectively correspond to the levels of aspartate aminotransferase, urea nitrogen, and creatine kinase.

The blood routine data of BALB/C mice in Table 5 and the blood biochemical data in FIG. 8 to FIG. 10 show that diketone compounds will not cause liver, kidney and blood toxicity after continuous treatment to healthy mice for 14 days at high concentration therapeutic doses.

Experimental Example 5 Evaluation on Compound's Cytotoxicity

In this experimental example, the toxicity of the compound BJMU-204 to cells was tested by an MTT method including the following specific steps.

(1) Logarithmic phase cells were collected, the concentration of a cell suspension was adjusted, the cell suspension was added to a cell culture plate in a dose of 100 μL per well, and the cells were then added to a cell culture plate so that the density of the cells to be tested was adjusted to 1000-10000 wells (edge wells were filled with sterile PBS).

(2) The cells were incubated at 37° C. in the presence of 5% $CO_2$ until the cells in a single layer covered the bottom of each well (96-well flat-bottom plate), and a drug in concentration gradients was added. Generally, the drug in 5 to 7 gradients was added in a dose of 100 μL per well, and 3 to 5 wells were set for each concentration of a drug.

(3) The cells were randomly divided into treated groups under light and treated groups in the dark, then incubated at 37° C. in the presence of 5% $CO_2$ for 16-48 h, and observed with an inverted microscope. Cells in the experimental photosensitizer-light irradiation group were incubated for 15 min and then irradiated with light. Cells in the control 5-α aminolevulinic acid (ALA)-light irradiation group were incubated for 3 h and then irradiated with light (the control drug ALA produced porphyrins for light absorption only after 3 h of incubation). MTT solution was added directly after the mice in the experimental photosensitizer-no light irradiation group were incubated for 15 min or after the mice in the control ALA-no light irradiation group were incubated for 3 h.

(4) For the experimental photosensitizer-light irradiation group, the cells were irradiated for 900 s with a laser having a wavelength of 450 nm to 480 nm (at an intensity of 110 $mW/cm^2$), and the final light dose was about 100 $J/cm^2$. After light irradiation, the cells were washed with PBS.

For the control ALA-light irradiation group, the cells were irradiated for 900 s with a laser having a wavelength of 630 nm to 650 nm (at an intensity of 110 $mW/cm^2$), and the final light dose was about 100 $J/cm^2$. After light irradiation, the cells were washed with PBS.

(5) MTT solution (5 mg/ml, 0.5% MTT) was added in a dose of 20 μL per well to further incubate the cells for 4 h. If the drug could react with the MTT, centrifuging was carried out first, and then the culture solution was discarded and the cells were carefully washed twice or three times with PBS, and then the culture solution containing MTT was added.

(6) The culture was terminated and the culture solution in the wells was carefully removed.

(7) Dimethyl sulfoxide was added in a dose of 150 μL per well, and the plate was then shaken on a shaker at a low speed for 10 min to fully dissolve crystals. The absorbance at OD 490 nm of each well was measured with enzyme-linked immunoassay.

(8) Zero adjustment wells (medium, MTT, dimethyl sulfoxide) and control wells (cells, dissolving media of the same concentration, culture solution, MTT, dimethyl sulfoxide) were set at the same time.

Figure 11:
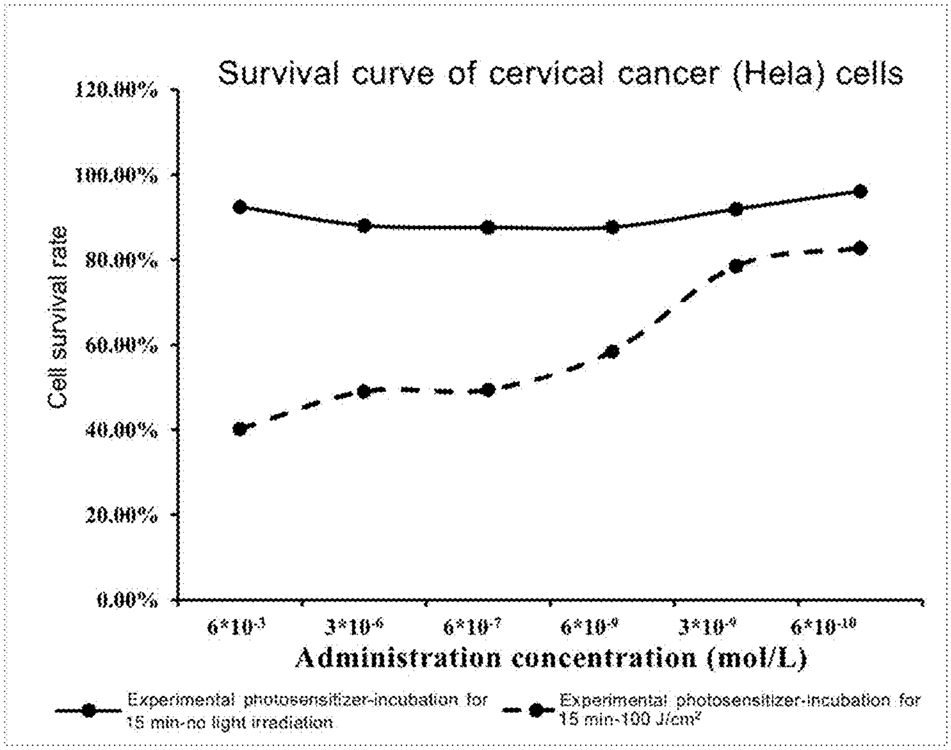
FIG. 11 shows the toxicity of experimental photosensitizer groups at different concentrations to human cervical cancer Hela cells in the dark and under light in Experimental Example 5. Administration concentrations are $6\times10^{-3}$ mol/L, $3\times10^{-6}$ mol/L, $6\times10^{-7}$ mol/L, $6\times10^{-9}$ mol/L, $3\times10^{-9}$ mol/L, and $6\times10^{-10}$ mol/L. As shown in the figure, when the diketone compound is given in the dark, its cytotoxicity to Hela is relatively low, indicating that the diketone compound has good safety. When the diketone compound is given under light, its cytotoxicity to Hela is relatively high, and the toxicity is significantly different from that of the diketone compound in the dark, indicating that the diketone compound has significant inhibitory activity to the tumor cell under light.

FIG. 11 shows the toxicity of experimental photosensitizer groups to human cervical cancer Hela cells in the dark and under light. Administration concentrations are $6\times10^{3}$ mol/L, $3\times10^{-6}$ mol/L, $6\times10^{7}$ mol/L, $6\times10^{-9}$ mol/L, $3\times10^{4}$ mol/L, and $6\times10^{-10}$ mol/L. The results show that the selected diketone compound of the disclosure has relatively low cytotoxicity to the human cervical cancer Hela cells when given in the dark. The above results indicate that the compound of the disclosure has good safety. The results show that the selected diketone compound of the disclosure has relatively high cytotoxicity to the human cervical cancer Hela cells when given under blue light. The above results indicate that the compound of the disclosure has significant inhibitory activity to the tumor cell under light.

Figure 12:
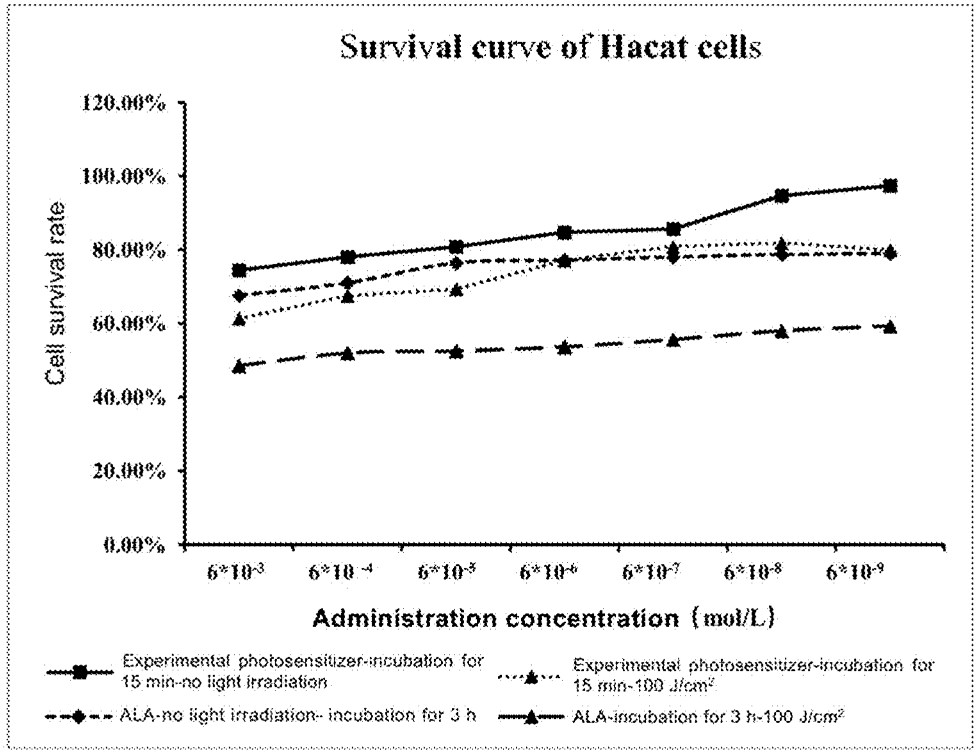
FIG. 12 shows the toxicity of experimental photosensitizer groups to human immortalized keratinocyte (Hacat cells) in the dark and under blue light and the toxicity of control drug 5-α aminolevulinic acid (ALA) groups to human immortalized keratinocyte (Hacat cells) in the dark and under red light in Experimental Example 5. Administration concentrations are $6\times10^{3}$ mol/L, $6\times10^{4}$ mol/L, $6\times10^{5}$ mol/L, $6\times10^{-6}$ mol/L, $6\times10^{-7}$ mol/L, $6\times10^{-8}$ mol/L, and $6\times10^{-9}$ mol/L. As shown in the figure, ALA is more toxic to normal cells under light. The toxicity of the diketone compound to normal cells under light is significantly different from the toxicity of ALA to normal cells under light. It indicates that, under light, the diketone compound is less toxic to normal cells and has high selectivity.

FIG. 12 shows the toxicity of experimental photosensitizer groups to human immortalized keratinocyte (Hacat cells) in the dark and under blue light and the toxicity of control drug ALA groups to human immortalized keratinocyte (Hacat cells) in the dark and under red light. Administration concentrations are $6\times10^{-3}$ mol/L, $6\times10^{-4}$ mol/L, $6\times10^{-5}$ mol/L, $6\times10^{-6}$ mol/L, $6\times10^{-7}$ mol/L, $6\times10^{-8}$ mol/L, and $6\times10^{-9}$ mol/L. The results show that the selected diketone compound of the disclosure has relatively low cytotoxicity to the human immortalized keratinocyte (Hacat cells) when given in the dark and under blue light. The control drug ALA has relatively high cytotoxicity to the human immortalized keratinocyte (Hacat cells) when given under red light. The toxicity of the selected diketone compound of the disclosure to normal cells under light is significantly different from the toxicity of ALA to normal cells under light. The above result indicates that, under light, the compound of the disclosure has low toxicity to normal cells and has high selectivity.

Experimental Example 6 Evaluation of Compound's Fluorescence on Mouse Skin

This experimental example evaluates the potential of compound BJMU-204 as a photosensitizer administrated to skin. Specific steps are as follows.

The BALB/C mice were depilated, and the skin was thoroughly cleaned, and then the mice were kept from light for more than 4 h. A small animal live imager IVIS SPECTRUM was used to take pictures of the backs of the mice and the excitation was carried out for 2 s at wavelengths of 480 nm and 520 nm. The mice not administered with the photosensitizer were photographed as a control. The mice with 100 μL of a 30% compound administrated to the skin (with a diameter of 10 mm) of the back were photographed and the fluorescence intensity was recorded, and then pictures were taken at 2 h, 4 h, 8 h, and 12 h after the administration of the compound. Each image was processed using Living Image 4.3.1, and average fluorescence in a circular field of view with a diameter of 10 mm on the skin was measured. Ambient light and the background fluorescence of mouse skin were corrected on the basis of fluorescence values of the backs of the mice without administration of the compound.

Figure 13:
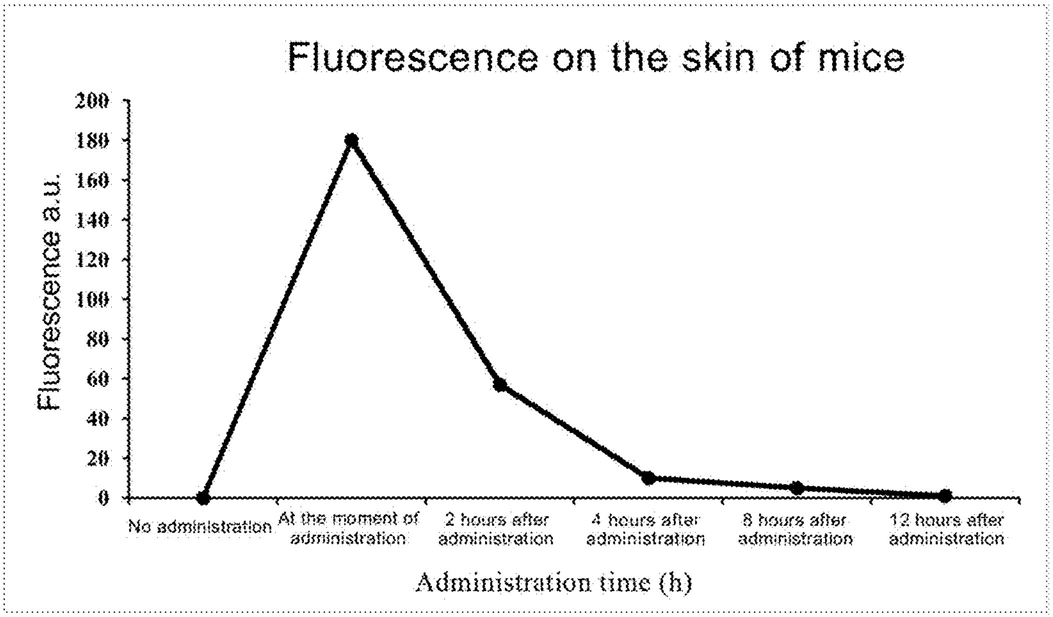
FIG. 13 shows that strong fluorescence is produced on the skin of mice in the experimental photosensitizer group under excitation of light at the moment of administration. Moreover, 4 hours after the administration, the fluorescence on the skin of mice decreases significantly. 8 hours after the administration, the fluorescence on the skin of mice is approaching zero. The above results indicate that the selected diketone compound of the disclosure can be used for photodynamic therapy or diagnosis on the skin. Moreover, the diketone compound metabolizes rapidly and does not stay in or out of the body for a long time, thus having good safety.

FIG. 13 shows that strong fluorescence is produced on the skin of mice in the experimental photosensitizer group under excitation of light at the moment of administration. The results indicate that the selected diketone compound of the disclosure can be used for photodynamic therapy or diagnosis on the skin. The diketone compound quickly produces fluorescence after being excited by light, and there is no need to wait for a long time. Moreover, 4 hours after the administration, the fluorescence on the skin of mice decreases significantly. 8 hours after the administration, the fluorescence on the skin of mice is approaching zero. The above results indicate that the compound of the disclosure is rapidly metabolized, does not stay in or out of the body for a long time, and has good safety.

The above experiments show that the selected diketone compound of the disclosure exhibits a significant killing activity to tumor cells under light, and exhibits a significant inhibitory activity to the growth of bacteria under light; in the dark, the diketone compound does not exhibit the two activities and has low toxicity. The selected diketone compound of the disclosure also significantly inhibits the activity of tumor cells in mice, and significantly enhances immune activity. In summary, the selected diketone compound of the disclosure can be used in photodynamic therapy to achieve the purpose of treating cancers, microorganism infections and related complications, and can also be used in the treatment of immune-related diseases.

While the specific embodiments of the disclosure have been described in detail, those skilled in the art will understand that according to all the teachings that have been disclosed, various modifications and substitutions can be made to those details, and these changes are all within the scope of the disclosure. The full scope of the disclosure is given by the appended claims and any equivalents thereof.

The invention claimed is:

1. A photodynamic method of treating a disease in a subject suffering from the disease, the method comprising administering a compound of Formula (I):

(I)

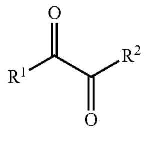

a pharmaceutically acceptable salt or ester, a stereoisomer, or a crystal form, or any combination or mixture thereof; and irradiating the subject with a light after the administering;

wherein the disease is selected from breast cancer, cervical cancer, colon cancer, and skin cancer; and wherein $R^1$ and $R^2$ of Formula (I) are each independently a linear or branched alkyl with 1 to 6 carbon atoms, a halogenated linear or branched alkyl with 1 to 6 carbon atoms, a hydroxyl group, or the following groups optionally substituted with one or more same or different substituents comprising aryl with 6 to 14 carbon atoms, 5- to 6-membered heteroaryl, 5- to 6-membered heterocyclyl, and 3- to 6-membered cycloalkyl, wherein the substituents are each independently selected from a hydroxyl group, a carboxyl group, a sulfonic group, a halogen atom, an amino group, a mercapto group, a nitro group, —C(O)O-(linear or branched alkyl with 1 to 4 carbon atoms), —$S(O)_2O$-(linear or branched alkyl with 1 to 4 carbon atoms), or —O-(linear or branched alkyl with 1 to 4 carbon atoms); and wherein the compound of Formula (I), a pharmaceutically acceptable salt or ester, a stereoisomer, or a crystal form, or any combination or mixture thereof is administered as the only active ingredient.

2. The method according to claim 1, wherein $R^1$ is selected from a linear or branched alkyl with 1 to 4 carbon atoms or an aryl with 6 to 14 carbon atoms; or wherein $R^2$ is selected from a linear or branched alkyl with 1 to 4 carbon atoms, a halogenated linear or branched alkyl with 1 to 4 carbon atoms, or hydroxy.

3. The method according to claim 1, wherein the compound is characterized in that (1) $R^1$ represents a linear or branched alkyl with 1 to 4 carbon atoms and $R^2$ represents a linear or branched alkyl with 1 to 4 carbon atoms;

(2) $R^1$ represents a linear or branched alkyl with 1 to 4 carbon atoms or a phenyl and $R^2$ represents a hydroxy;

(3) $R^1$ represents a linear or branched alkyl with 1 to 4 carbon atoms and $R^2$ represents a halogenated linear or branched alkyl with 1 to 4 carbon atoms;

(4) $R^1$ and $R^2$ each represent a phenyl, and the phenyl is optionally substituted with one or more substituents which are the same or different; or (5) $R^1$ and $R^2$ are each independently a nitrogen-containing 5- to 6-membered heteroaryl, and the nitrogen-containing 5- to 6-membered heteroaryl is optionally substituted with one or more substituents which are the same or different.

4. The method according to claim 1, wherein the compound is selected from the following:

| No. | Structural formula |
|---|---|
| BJMU-201 | 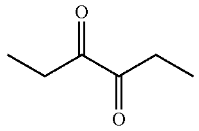 |
| BJMU-202 | 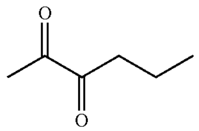 |

-continued

| No. | Structural formula |
|---|---|
| BJMU-203 | 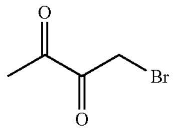 |
| BJMU-204 | 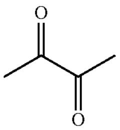 |
| BJMU-205 | 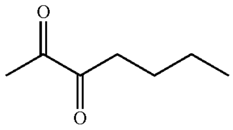 |
| BJMU-206 | 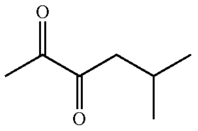 |
| BJMU-207 | 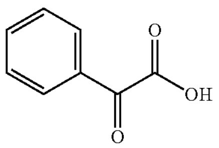 [SMILES: O=C(O)C(=O)c1ccccc1] |
| BJMU-208 | 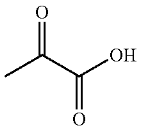 |
| BJMU-209 | 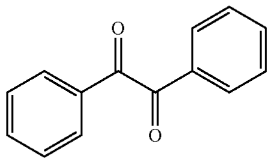 [SMILES: O=C(C(=O)c1ccccc1)c1ccccc1] |
| BJMU-210 | 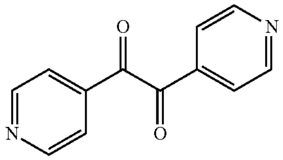 [SMILES: O=C(C(=O)c1ccncc1)c1ccncc1] |
| BJMU-211 | 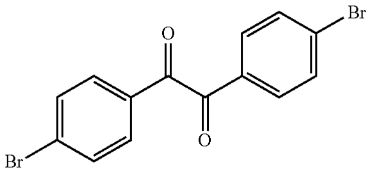 [SMILES: O=C(C(=O)c1ccc(Br)cc1)c1ccc(Br)cc1] |
| BJMU-212 | 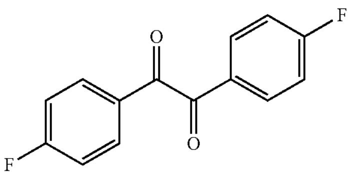 [SMILES: O=C(C(=O)c1ccc(F)cc1)c1ccc(F)cc1] |

-continued

| No. | Structural formula |
|---|---|
| BJMU-213 | 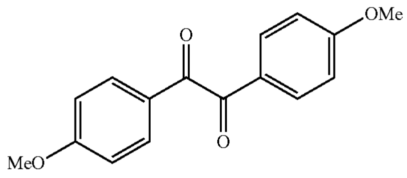 [SMILES: COc1ccc(C(=O)C(=O)c2ccc(OC)cc2)cc1] |
| BJMU-214 | 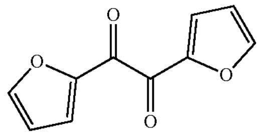 [SMILES: O=C(C(=O)c1ccco1)c1ccco1] . |

5. The method according to claim 1, wherein the method is characterized by one or more of the following:

(1) the light being a single-wavelength light or a mixed light;

(2) at least part of the wavelength of the light being in a range of 10 nm to 1 mm;

(3) irradiating for 1 s to 12 h; or (4) irradiating at a light density of 1 to 2000 $mW/cm^2$.

6. The photodynamic method of claim 1, wherein the linear or branched alkyl with 1 to 6 carbon atoms is a linear or branched alkyl with 1 to 4 carbon atoms;

wherein the aryl with 6 to 14 carbon atoms is a phenyl or a naphthyl;

wherein the halogenated linear or branched alkyl with 1 to 6 carbon atoms is a fluoro-, chloro-, bromo- or iodo-linear or branched alkyl with 1 to 6 carbon atoms;

wherein the 5- to 6-membered heteroaryl contains 1 to 3 ring atoms selected from nitrogen, oxygen, and sulfur; or wherein the 5- to 6-membered heterocyclyl contains 1 to 3 ring atoms selected from nitrogen, oxygen, and sulfur.

7. The photodynamic method of claim 1, wherein the linear or branched alkyl with 1 to 6 carbon atoms is methyl, ethyl, n-propyl, isopropyl, n-butyl, sec-butyl, isobutyl, or tert-butyl.

8. The photodynamic method according to claim 1, wherein $R^1$ is methyl, ethyl or phenyl; or wherein $R^2$ is selected from the group consisting of methyl, ethyl, n-propyl, isopropyl, n-butyl, tert-butyl, bromomethyl, bromoethyl, and hydroxy.

9. The photodynamic method according to claim 1, wherein the skin cancer is non-melanoma skin cancer or melanoma.

10. The photodynamic method according to claim 9, wherein the non-melanoma skin cancer is squamous cell carcinoma.

11. A photodynamic method of treating a disease in a subject suffering from the disease, the method comprising administering a compound of Formula (I):

(I)

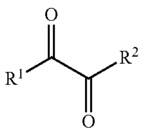

a pharmaceutically acceptable salt or ester, a stereoisomer, or a crystal form, or any combination or mixture thereof; and irradiating the subject with a light after the administering;

wherein the disease is related to a microorganism infection, and the microorganism is selected from human papilloma virus, *Propionibacterium acnes* and *Escherichia coli*; and wherein $R^1$ and $R^2$ of Formula (I) are each independently a linear or branched alkyl with 1 to 6 carbon atoms, a halogenated linear or branched alkyl with 1 to 6 carbon atoms, a hydroxyl group, or the following groups optionally substituted with one or more same or different substituents comprising aryl with 6 to 14 carbon atoms, 5- to 6-membered heteroaryl, 5- to 6-membered heterocyclyl, and 3- to 6-membered cycloalkyl, wherein the substituents are each independently selected from a hydroxyl group, a carboxyl group, a sulfonic group, a halogen atom, an amino group, a mercapto group, a nitro group, —C(O)O-(linear or branched alkyl with 1 to 4 carbon atoms), —$S(O)_2O$-(linear or branched alkyl with 1 to 4 carbon atoms), or —O-(linear or branched alkyl with 1 to 4 carbon atoms); and wherein the compound of Formula (I), a pharmaceutically acceptable salt or ester, a stereoisomer or a crystal form, or any combination or mixture thereof is administered as the only active ingredient.

12. The method according to claim 11, wherein the compound is selected from the following:

| No. | Structural formula |
| --- | --- |
| BJMU-201 | 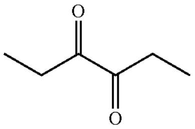 |
| BJMU-202 | 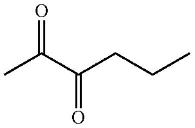 |
| BJMU-203 | 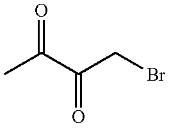 |
| BJMU-204 | 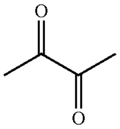 |
| BJMU-205 | 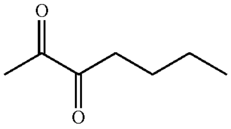 |
| BJMU-206 | 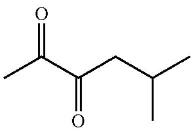 |

-continued

| No. | Structural formula |
| --- | --- |
| BJMU-207 | 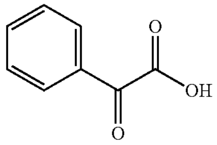 [SMILES: O=C(O)C(=O)c1ccccc1] |
| BJMU-208 | 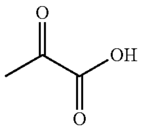 |
| BJMU-209 | 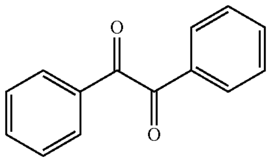 [SMILES: O=C(C(=O)c1ccccc1)c1ccccc1] |
| BJMU-210 | 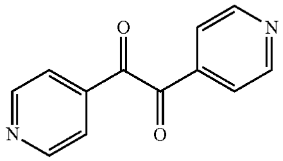 [SMILES: O=C(C(=O)c1ccncc1)c1ccncc1] |
| BJMU-211 | 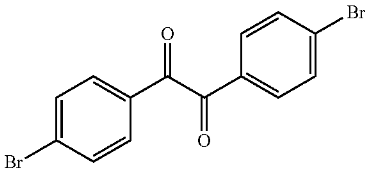 [SMILES: O=C(C(=O)c1ccc(Br)cc1)c1ccc(Br)cc1] |
| BJMU-212 | 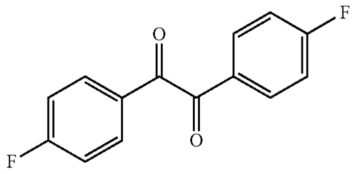 [SMILES: O=C(C(=O)c1ccc(F)cc1)c1ccc(F)cc1] |
| BJMU-213 | 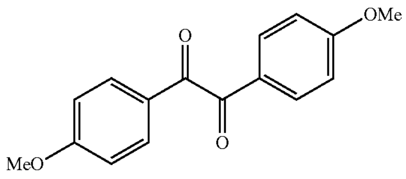 [SMILES: COc1ccc(C(=O)C(=O)c2ccc(OC)cc2)cc1] |
| BJMU-214 | 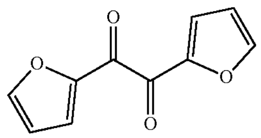 |

.

13. The method according to claim 11, wherein the method is characterized by one or more of the following:

(1) the light being a single-wavelength light or a mixed light;

(2) at least part of the wavelength of the light being in a range of 10 nm to 1 mm;

(3) irradiating for 1 s to 12 h; or (4) irradiating at a light density of 1 to 2000 $mW/cm^2$.

* * * * *